(12) United States Patent
Galley et al.

(10) Patent No.: US 9,136,939 B2
(45) Date of Patent: *Sep. 15, 2015

(54) GRAPHICAL USER INTERFACE PERTAINING TO A BOLUS CALCULATOR RESIDING ON A HANDHELD DIABETES MANAGEMENT DEVICE

(75) Inventors: Paul J. Galley, Cumberland, IN (US); Mark G. Mears, Westfield, IN (US); Phillip E. Pash, Indianapolis, IN (US); Vincent R. Rizzo, Indianapolis, IN (US); Bettina Steiner, Kaiserstuhl (CH); Kristin M. Westerfield, Indianapolis, IN (US); Richard W. Wilson, Fortville, IN (US)

(73) Assignee: Roche Diabetes Care, Inc., Indianapolis, IN (US)

( * ) Notice: Subject to any disclaimer, the term of this patent is extended or adjusted under 35 U.S.C. 154(b) by 16 days.

This patent is subject to a terminal disclaimer.

(21) Appl. No.: 13/595,202

(22) Filed: Aug. 27, 2012

(65) Prior Publication Data

US 2013/0172707 A1 Jul. 4, 2013

Related U.S. Application Data

(60) Provisional application No. 61/581,149, filed on Dec. 29, 2011.

(51) Int. Cl.
*G06Q 50/22* (2012.01)
*H04B 7/26* (2006.01)
(Continued)

(52) U.S. Cl.
CPC ............... *H04B 7/26* (2013.01); *A61B 5/0002* (2013.01); *A61B 5/14532* (2013.01);
(Continued)

(58) Field of Classification Search
CPC .............. G06F 19/3468; G06F 19/322; G06F 19/3418; G06F 19/3487; G06F 19/3406; A61B 5/7435; A61B 5/0002; A61B 5/14532; H04W 84/18; H04W 84/20; A61M 5/14244; A61M 5/1723; A61M 2205/35; A61M 2205/3569; A61M 2205/3584; H04B 7/26
USPC ........ 700/266, 17, 18, 83; 702/19, 31, 32, 22; 600/365, 347
See application file for complete search history.

(56) References Cited

U.S. PATENT DOCUMENTS

| | | | |
|---|---|---|---|
| 5,840,020 | A | 11/1998 | Heinonen et al. |
| 5,971,922 | A | 10/1999 | Arita et al. |

(Continued)

FOREIGN PATENT DOCUMENTS

| | | |
|---|---|---|
| WO | WO2009048462 | 4/2009 |
| WO | WO2011/033509 | 3/2011 |
| WO | WO2012/049291 | 4/2012 |

OTHER PUBLICATIONS

Insulin Bolus Calculater, Nationwide Children's: p. 1, 2014.*

*Primary Examiner* — Shogo Sasaki
(74) *Attorney, Agent, or Firm* — Harness, Dickey

(57) ABSTRACT

A handheld diabetes manager is presented with an improved graphical user interface for a bolus calculator. The bolus calculator is configured to receive blood glucose measurements from a blood glucose measurement module and operates, in response to an input, to compute an insulin recommendation for a patient based in part on the blood glucose measurements. The graphical user interface for the bolus calculator includes a health adjustment screen that enables a user to input a value for health events associated with the insulin recommendation, where the input value represents a cumulative effect of the health events on insulin of the patient and the health adjustment screen presents a different icon for each of the health events associated with the insulin recommendation.

5 Claims, 24 Drawing Sheets

(51) Int. Cl.
    *A61B 5/00*     (2006.01)
    *A61B 5/145*    (2006.01)
    *A61M 5/142*    (2006.01)
    *A61M 5/172*    (2006.01)
    *G06F 19/00*    (2011.01)
    *H04W 4/00*     (2009.01)
    *H04W 84/20*    (2009.01)

(52) U.S. Cl.
    CPC ......... *A61B 5/7435* (2013.01); *A61M 5/14244* (2013.01); *A61M 5/1723* (2013.01); *G06F 19/3406* (2013.01); *G06F 19/3468* (2013.01); *H04W 4/001* (2013.01); *A61M 2205/35* (2013.01); *A61M 2205/3569* (2013.01); *A61M 2205/3584* (2013.01); *H04W 84/20* (2013.01)

(56)　　　　　References Cited

U.S. PATENT DOCUMENTS

| | | | |
|---|---|---|---|
| 7,291,107 | B2 | 11/2007 | Hellwig et al. |
| 7,553,281 | B2 | 6/2009 | Hellwig et al. |
| 7,912,655 | B2 | 3/2011 | Power et al. |
| 7,976,467 | B2 | 7/2011 | Young et al. |
| 8,118,770 | B2 | 2/2012 | Galley et al. |
| 8,226,891 | B2 | 7/2012 | Sloan et al. |
| 2004/0172284 | A1 | 9/2004 | Sullivan et al. |
| 2005/0192494 | A1 | 9/2005 | Ginsberg |
| 2006/0047192 | A1 | 3/2006 | Hellwig et al. |
| 2006/0137695 | A1 | 6/2006 | Hellwig et al. |
| 2008/0058628 | A1 | 3/2008 | Hellwig et al. |
| 2008/0139910 | A1 | 6/2008 | Mastrototaro et al. |
| 2008/0183060 | A1 | 7/2008 | Steil et al. |
| 2008/0312585 | A1 | 12/2008 | Brukalo et al. |
| 2009/0006061 | A1* | 1/2009 | Thukral et al. ................ 703/11 |
| 2009/0030733 | A1 | 1/2009 | Cohen et al. |
| 2009/0036753 | A1 | 2/2009 | King |
| 2009/0105570 | A1 | 4/2009 | Sloan et al. |
| 2009/0113295 | A1 | 4/2009 | Halpern et al. |
| 2009/0305317 | A1 | 12/2009 | Brauer et al. |
| 2010/0057043 | A1 | 3/2010 | Kovatchev et al. |
| 2010/0081911 | A1 | 4/2010 | Sloan et al. |
| 2010/0105999 | A1 | 4/2010 | Dixon et al. |
| 2010/0160740 | A1 | 6/2010 | Cohen et al. |
| 2010/0160757 | A1 | 6/2010 | Weinert et al. |
| 2010/0160759 | A1 | 6/2010 | Celentano et al. |
| 2010/0168660 | A1 | 7/2010 | Galley et al. |
| 2010/0204557 | A1 | 8/2010 | Kiaie et al. |
| 2010/0212675 | A1 | 8/2010 | Walling et al. |
| 2010/0218132 | A1 | 8/2010 | Soni et al. |
| 2010/0249530 | A1 | 9/2010 | Rankers et al. |
| 2010/0256047 | A1 | 10/2010 | Sieh et al. |
| 2010/0317953 | A1 | 12/2010 | Reggiardo et al. |
| 2010/0331650 | A1 | 12/2010 | Batman et al. |
| 2010/0331654 | A1 | 12/2010 | Jerdonek et al. |
| 2011/0178717 | A1 | 7/2011 | Goodnow et al. |
| 2011/0193704 | A1 | 8/2011 | Harper et al. |
| 2011/0237917 | A1 | 9/2011 | Roy et al. |
| 2012/0266251 | A1 | 10/2012 | Birtwhistle et al. |

\* cited by examiner

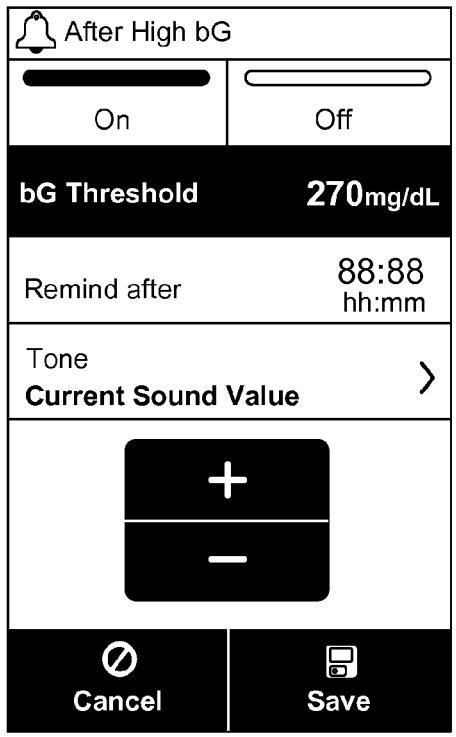
FIG. 3D
FIG. 3E

GRAPHICAL USER INTERFACE PERTAINING TO A BOLUS CALCULATOR RESIDING ON A HANDHELD DIABETES MANAGEMENT DEVICE

CROSS-REFERENCE TO RELATED APPLICATION

This application claims the benefit of U.S. Ser. No. 61/581,149 filed Dec. 29, 2011. The disclosure of the above application is incorporated herein by reference.

FIELD

This disclosure relates generally to a graphical user interface for a bolus calculator residing on a handheld diabetes management device.

BACKGROUND

Diabetes mellitus, often referred to as diabetes, is a chronic condition in which a person has elevated blood glucose levels that result from defects in the body's ability to produce and/or use insulin. There are three main types of diabetes. Type 1 diabetes usually strikes children and young adults, and may be autoimmune, genetic, and/or environmental. Type 2 diabetes accounts for 90-95% of diabetes cases and is linked to obesity and physical inactivity. Gestational diabetes is a form of glucose intolerance diagnosed during pregnancy and usually resolves spontaneously after delivery.

In 2009, according to the World Health Organization, at least 220 million people worldwide suffer from diabetes. In 2005, an estimated 1.1 million people died from diabetes. Its incidence is increasing rapidly, and it is estimated that between 2005 and 2030, the number of deaths from diabetes will double. In the United States, nearly 24 million Americans have diabetes with an estimated 25 percent of seniors age 60 and older being affected. The Centers for Disease Control and Prevention forecast that 1 in 3 Americans born after 2000 will develop diabetes during their lifetime. The National Diabetes Information Clearinghouse estimates that diabetes costs $132 billion in the United States alone every year. Without treatment, diabetes can lead to severe complications such as heart disease, stroke, blindness, kidney failure, amputations, and death related to pneumonia and flu.

Management of diabetes is complex as the level of blood glucose entering the bloodstream is dynamic. The variation of insulin that controls the transport of glucose out of the bloodstream also complicates diabetes management. Blood glucose levels are sensitive to diet and exercise, but also can be affected by sleep, stress, smoking, travel, illness, menses, and other psychological and lifestyle factors unique to individual patients. The dynamic nature of blood glucose and insulin, and all other factors affecting blood glucose, often require a person with diabetes to understand ongoing patterns and forecast blood glucose levels (or at least understand the actions that raise or lower glucose in the body). Therefore, therapy in the form of insulin or oral medications, or both, can be timed to maintain blood glucose levels in an appropriate range.

Management of diabetes is often highly intrusive because of the need to consistently obtain reliable diagnostic information, follow prescribed therapy, and manage lifestyle on a daily basis. Daily diagnostic information, such as blood glucose, is typically obtained from a capillary blood sample with a lancing device and is then measured with a handheld blood glucose meter. Interstitial glucose levels may be obtained from a continuous glucose sensor worn on the body. Prescribed therapies may include insulin, oral medications, or both. Insulin can be delivered with a syringe, an insulin pen, an ambulatory infusion pump, or a combination of such devices. With insulin therapy, determining the amount of insulin to be injected can require forecasting meal composition of carbohydrates, fat and proteins along with effects of exercise or other physiologic states. The management of lifestyle factors such as body weight, diet, and exercise can significantly influence the type and effectiveness of a therapy.

Handheld diabetes management devices are commonly used to manage diabetes care of patients. In some instances, these types of devices may be configured to provide insulin therapy recommendations. There is a need to provide even more accurate insulin recommendations to the user based on various user inputs that take into account current activities and a current health of the user, and which is also highly customizable by the user to thus enhance the accuracy, convenience and efficiency of the device in generating a recommended bolus or a suggested carbohydrate amount for the user. Moreover, during treatment more knowledgeable patients may wish to modify or override treatment recommendations. Thus, there is a need for a more effective means for a patient to modify treatment recommendations.

The statements in this section merely provide background information related to the present disclosure and may not constitute prior art.

SUMMARY

In one aspect of the disclosure, a computer-implemented method is provided for determining a bolus recommendation which accounts for multiple health events. The method includes: receiving indicia for one or more health events to be associated with a request for an insulin recommendation; receiving a request for an insulin recommendation for a patient; determining how many health events are associated with the request for an insulin recommendation; prompting the user for an input for the health events associated with the insulin recommendation, where the prompting is in response to a determination that two or more health events are associated with the request for an insulin recommendation and the input represents a cumulative effect of the health events on the insulin on the patient; receiving an input value from the user in response to the prompting; and computing an insulin recommendation for the patient using the input value. The user may be prompted by a health adjustment screen which displays an icon for each of the health events associated with the insulin recommendation.

An insulin recommendation is based in part on recent blood glucose measures. Upon receipt of a blood glucose measure, a countdown timer is initiated. Before the countdown timer expires, the insulin recommendation function is enabled; whereas, the insulin recommendation function is disabled after the expiration of the countdown timer. The countdown timer may be displayed on one or more user interfaces associated with the bolus calculator.

An insulin recommendation presented to the user includes a correction amount, a meal amount and a total amount of insulin, where the correction amount is intended to lower a patient's blood glucose level to a target value, the meal amount is intended to compensate for carbohydrates consumed by the patient and the total amount is equal to a sum of the correction amount and the meal amount. Adjustments made to the correction amount and the meal amount are reflected in the total amount and vice versa.

In another aspect of the disclosure, an improved graphical user interface is provided for a bolus calculator residing on a handheld diabetes management device. The device includes: a port configured to receive a test strip having a reaction site for receiving a sample of blood from a patient; a blood glucose measurement module cooperatively operable with a test strip inserted in the port to measure glucose in a sample of blood residing on the test strip; and a bolus calculator module configured to receive blood glucose measurements from the blood glucose measurement module and operates, in response to an input, to compute an insulin recommendation for a patient based in part on the blood glucose measurements. A user interface module in data communication with the bolus calculator module presents a graphical user interface on a display of the diabetes manager, wherein the graphical user interface includes a health adjustment screen that enables a user to input a value for health events associated with the insulin recommendation, the input value represents a cumulative effect of the health events on insulin of the patient and the health adjustment screen presents a different icon for each of the health events associated with the insulin recommendation.

Further areas of applicability will become apparent from the description provided herein. It should be understood that the description and specific examples are intended for purposes of illustration only and are not intended to limit the scope of the present disclosure.

BRIEF DESCRIPTION OF THE DRAWINGS

The following figures are selected embodiments of the handheld diabetes manager with enhanced data capability and related system embodiments and information.

FIGS. 3B-3E illustrate exemplary graphical user interfaces associated with obtaining a blood glucose measure using the device;

Figure 1:
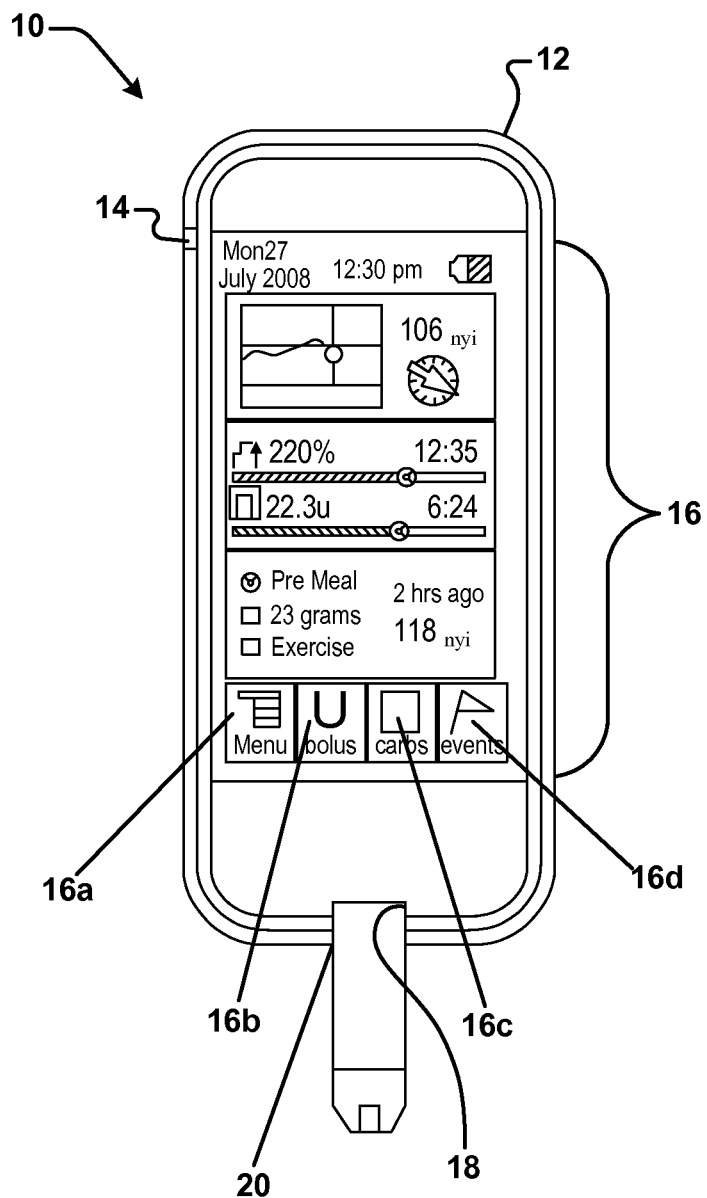
FIG. 1 is a perspective view of one embodiment of a handheld diabetes bG management device in accordance with the present disclosure.

The drawings described herein are for illustrative purposes only of selected embodiments and not all possible implementations, and are not intended to limit the scope of the present disclosure. Corresponding reference numerals indicate corresponding parts throughout the several views of the drawings.

DETAILED DESCRIPTION

Referring to FIG. 1, there is shown a high level drawing of one embodiment of a handheld, diabetes management device 10 that may be used in measuring the blood glucose (bG) of a patient and implementing a bolus calculation or carbohydrate suggestion. Typically the device 10 includes a housing 12 that may contain user unit control switches 14 (e.g., ON/OFF), a touchscreen display 16, and a port 18 into which a bG test strip 20 may be inserted. The display 16 may display user selectable options for allowing the user to access a software driven menu 16a of various selections, a selection 16b for allowing the user to enter bolus information, a selection 16c for enabling the user to enter carbohydrate information for snacks or meals, and a selection 16d for allowing the user to enter information pertaining to health events (e.g., meals, exercise, periods of stress, periodic physiological events such as a menstrual cycle, etc.) that may affect the user's bG measurement being read by the device 10. Although the display 16 will be described herein as a touchscreen input, it will be appreciated that any other suitable form of input for the display may be incorporated (e.g., buttons, mouse, etc.). If a touchscreen display is not used, the user control switches 14 may need to include specific buttons or controls by which the user is able to select various options and input markers needed to carry out the bolus calculation or carbohydrate suggestion. It will be appreciated that the above is a high level description of the device 10, and in practice the device may include additional controls, input ports, output ports, etc., as may be desired to even further enhance the utility of the device 10 or its use with other components and devices (e.g., laptop computers, infusion pumps, etc.). Accordingly, the above description of the device 10 should not be taken as limiting its construction or features in any way.

Figure 2:
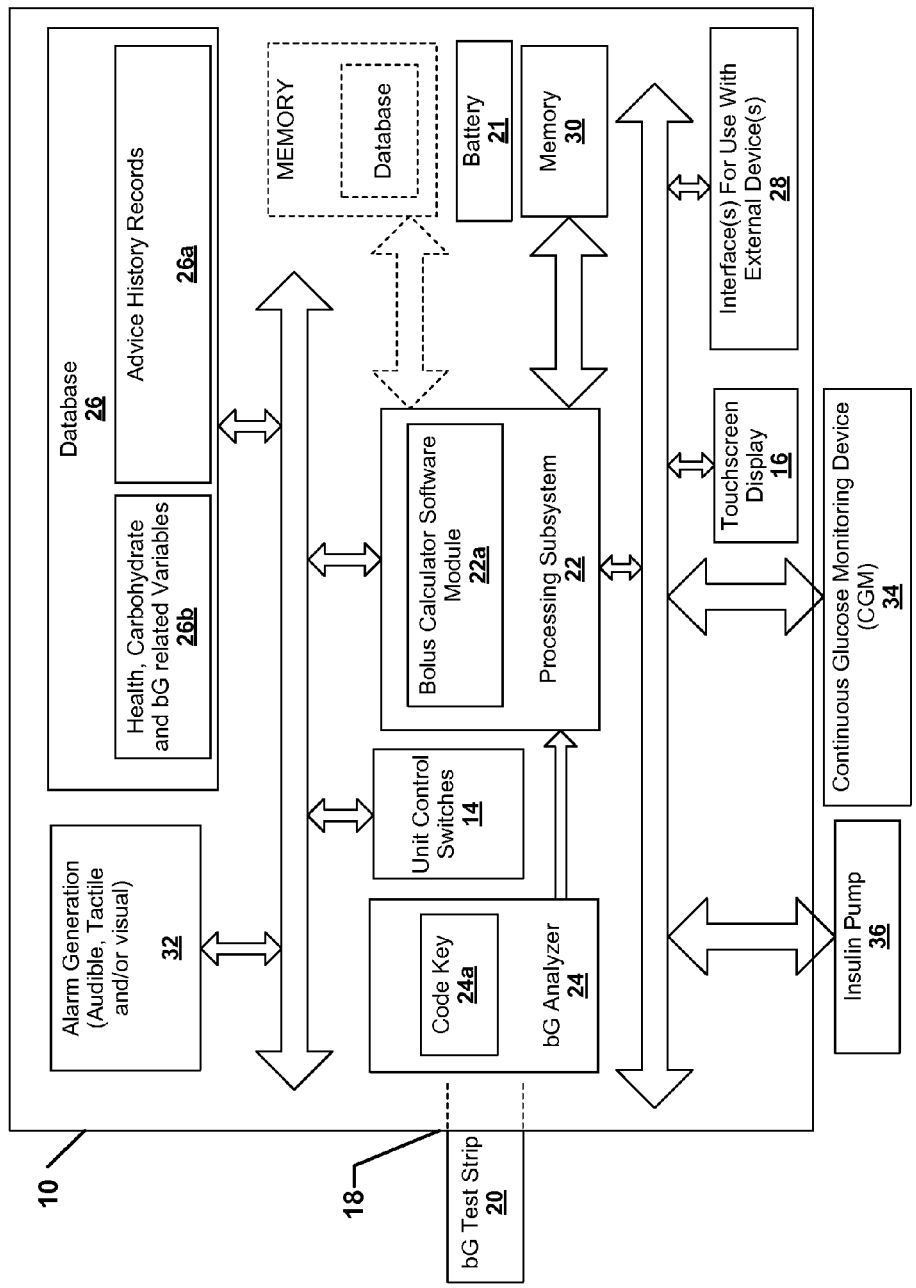
FIG. 2 is a high level block diagram of various components and subsystems that may be incorporated in the device shown in FIG. 1.

Referring to FIG. 2, a high level block diagram of the device 10 is shown. The device 10 can include a rechargeable or non-rechargeable battery 21 for powering the various electronic components of the device 10. A processing subsystem 22 (e.g., a microprocessor based subsystem) is included that receives information from a bG analyzer 24. The bG analyzer 24 is located adjacent the port 18 of the housing 12 to permit the bG analyzer 24 to read the bG test strip 20. The bG analyzer 24 can include a code key 24a that includes calibration information for the bG test strip 20 being read. The processing subsystem 22 can also be in communication with a database 26 that is used to store bG test values obtained from the bG analyzer 24 and other important health related information for the user. In particular, the database 26 can include a subsection 26a for storing recommended bolus and carbohydrate advice history records (hereinafter "advice history records") that are still active in their influence of current and future advice, and a section 26b for storing medication (insulin), health, carbohydrate and bG related variables (e.g., insulin sensitivities of the user for various time segments of the day) pertinent to the user. It will be appreciated that the database 26 will be formed by a non-volatile memory. Further, the related variables such as the insulin sensitivities of the user can be stored as global parameters and may not be in the advice history records.

The processing subsystem 22 can also be in communication with the display 16, the user control switches 14, and one or more interfaces 28 for interfacing the device 10 to other external devices. The processing subsystem 22 can also be in communication with a memory (such as a RAM) 30 for storing various types of information (e.g., meal and bed times) that are input by the user, as well as any other information requiring temporary or permanent storage. However, it will be appreciated that the database 26 and the memory 30 could be implemented in a single memory device (e.g., RAM) if desired, as indicated in phantom in FIG. 2. The processing subsystem 22 can be in communication with an alarm generation subsystem 32 that is used to generate an alarm consisting of audible signals, tactile signals (e.g., a vibration signal) or possibly even visual signals such as illuminated lights (e.g., LEDs) on the device 10. The processing subsystem 22 can also receive inputs from a remote continuous glucose monitoring ("CGM") device 34 secured to the user's body such that device 10 is continually updated with glucose information for the user. Finally the processing subsystem 22 can be in communication with a remote insulin infusion pump 36 (herein referred to as an "insulin pump 36") being worn by the user so that the device 10 is able to communicate bolus information to the insulin pump 36. By "remote" it is meant that the CGM device 34 and the insulin pump 36 are each located outside of the device 10 but otherwise still in communication with the device 10. It should be appreciated that the device 10 can communicate with the insulin pump 36 either through a wired or wireless connection.

The device 10 can be used to implement a non-transitory machine readable code, for example a bolus calculator software module 22a (herein referred to as "bolus calculator 22a"), that is run by the processing subsystem 22. The bolus calculator 22a can be formed as a single module or as a collection of independent modules that run concurrently on the processing subsystem 22. The processing subsystem 22, working in connection with the bolus calculator 22a, receives a wide variety of user inputs applied by the user through the touchscreen display 16 to generate a recommended correction bolus, a recommended meal bolus, a recommended total bolus, or when appropriate a suggested carbohydrate amount. The suggested carbohydrate amount may be provided in response to the detection by the device 10 of a hypoglycemic bG test value. The operations and capabilities of the device 10 will be explained in detail in the following paragraphs. The device 10 significantly enhances the convenience and ease of use to the user through the implementation of a plurality of customizable inputs that enable the user to program the device 10 with unique health information pertinent to the user. More specifically, the device 10 allows the user to program the device 10 with health information which even more completely enables the device 10 to take into account unique health conditions affecting the user, as well as regular occurring and non-regular occurring health events that could otherwise have an impact on the bolus and carbohydrate calculations made by the device 10.

In an example embodiment, the bolus calculator 22a is configured to generate advice history records which are indicative of the bolus and carbohydrate calculations and bolus recommendations made by the device 10. The bolus calculator 22a may be further configured to include data indicative of a patient's adherence or variance from the recommendations in the advice history records. In some embodiments, an advice history record can include a plurality of fields, including a time field that defines a time of the advice history record, a test flag field, a record content field indicating one or more types of events defined in the advice history record, and one or more fields defining values corresponding to the events indicated in the record content field.

In an exemplary embodiment, the advice history record includes a time field. The time field denotes a time corresponding to the advice history record. The time can include values indicating a year, a month, a day, an hour, and a minute of the advice history record. It should be appreciated that the time field can be divided into a plurality of subfields for each of the values. When a new advice history record is generated, the time at which the advice history record was generated populates the time field.

In an exemplary embodiment, the test flag field indicates results of one or more tests. The test field may include test flags corresponding to the one or more tests. As should be appreciated, a test flag can be a bit that is set to 1 if the result is true and 0 if the result is false. The test flags can include a HI test flag that indicates whether a bG concentration value is outside of an upper range of values that can be displayed by the device 10. When the HI value is set to 1, the HI test flag indicates that a bG concentration value in above the range of bG concentration values that can be displayed by the device 10. The test flags can further include a LO test flag. When the LO test flag is set to 1, the LO test flag indicates that the bG concentration value is below the range of values that can be displayed by the device 10. The test flags can also include a HYPO test flag. When the HYPO test flag is set to 1, the HYPO test flag indicates that the bG concentration value of the patient corresponds to a hypoglycemic state or is below the lower end of a target range. It is appreciated that the test field may include additional test flags.

As mentioned, the record content field indicates one or more types of events defined in the advice history record or that certain conditions relating to the events were met. The different types of events can include a blood glucose concentration, a carbohydrate amount associated with food intake of the patient, a health percentage value selected by the user, an insulin amount was recommended to the patient, a confirmation that insulin was administered to the patient, a confirmation that a bolus recommendation was accepted by the patient, an indication that a correction bolus was administered, and an indication that a meal bolus was recommended to the patient. As should be appreciated, if one or more events are indicated in the record content field of the advice history record, the corresponding fields in the advice history record are populated with values.

In an exemplary embodiment, the advice history record includes a bG concentration field. The bG concentration field is populated with a valid value when the record content field indicates that a bG concentration value has been associated with the advice history record. The bG concentration value indicates a bG concentration value from a bG measurement performed by the device 10 or was otherwise provided by the patient. It should be appreciated that the bG concentration value can be represented in mg/dL or mmol/L.

In an exemplary embodiment, the advice history record includes a carbohydrate amount field. The carbohydrate amount field is populated with a valid value when the record content field indicates that a carbohydrate amount value has been associated with the advice history record. A carbohydrate amount value is an amount of carbohydrates that a patient consumed in a recent food intake. As will be discussed in further detail below the carbohydrate amount value can be greater than or less than a "snack size" threshold. When the carbohydrate amount value is greater than the "snack size" threshold the food intake is considered a meal as opposed to a snack. The carbohydrate value can be provided by the patient via the user interface of the device 10 and can be represented, for example in grams.

In an exemplary embodiment, the advice history record includes a health percentage amount. The health percentage amount field is populated with a valid value when the record content field indicates that one or more health percentages have been associated with the advice history record. As discussed above, the user can enter different health events, e.g., exercise, periods of stress, and periodic physiological events such as a menstrual cycle or a custom health event. The patient or another user can provide percentages representing an amount of effect that the health event has on increasing or decreasing the bG concentration (or insulin need) of the patient.

In an exemplary embodiment, the advice history record includes a correction bolus field. The correction bolus field is populated with a valid value when the record content field indicates that a non-null correction bolus amount has been associated with the advice history record. The correction bolus amount indicates a bolus amount selected by a patient to either decrease or increase a bG concentration value. A negative bolus amount corresponds to a scenario where the patient's bG concentration is below a target bG value and a positive bolus amount corresponds to a scenario where the patient's bG concentration is above the target bG value. It is noted that in some embodiments, the correction bolus field is populated when the user overrides a correction bolus recommendation provided by the bolus calculator 22a.

In an exemplary embodiment, the advice history record includes a meal bolus field. The meal bolus field is populated with a valid value when the record content field indicates that a non-null meal bolus amount has been associated with the advice history record. The meal bolus amount indicates a bolus amount selected by a patient to offset the effects of a meal, e.g., carbohydrate intake. In some embodiments, the meal bolus field is populated when the user overrides a meal bolus recommendation provided by the bolus calculator 22a.

In an exemplary embodiment, the advice history record includes a confirmed correction bolus field. The confirmed correction bolus field is populated with a valid value when the record content field indicates that a confirmed insulin amount and a non-null correction bolus amount has been associated with the advice history record. The confirmed correction bolus amount indicates a bolus amount that was delivered to the patient by an insulin pump 36 in response to a patient-saved correction bolus.

In an exemplary embodiment, the advice history record includes a confirmed meal bolus field. The confirmed meal bolus field is populated with a valid value when the record content field indicates that a confirmed insulin amount and a non-null meal bolus amount have been associated with the advice history record. The confirmed meal bolus amount indicates a bolus amount that was delivered to the patient by an insulin pump 36 in response to a patient-saved meal bolus.

It should be appreciated that the advice history record may include variations of the fields described above or alternative or additional fields. The fields of the advice history record provided are provided for example only and not intended to be limiting.

In some embodiments, the advice history record may include one or more different parameter values relating to events defined in the advice history record. For example, the advice history record may include a target value, a meal rise value, an offset time, and an acting time value. The target value is a target bG level of the patient. The target value can be represented as a function of an upper and lower limit for the patient's bG levels. The meal rise value is an amount by which the bG level of a patient may increase with respect to the target value as a result of a carbohydrate intake. In some embodiments, the meal rise value is a function of time and the administration of insulin, such that the meal rise remains constant for a first predetermined amount of time after the patient is administered insulin, i.e., offset time, and then decreases linearly after the first predetermined amount of time. The total amount of time that a dose of insulin has an effect on the bG levels of a patient is the acting time. As will be discussed later, if the meal rise value as a result of the effect of a dose of insulin is graphed, the result is referred to as an action shape. In some embodiments, the action shape is a trapezoid, such that the offset time defines the shorter base and the acting time defines the longer base. Other parameters that may be included in the advice history record may include a carb ratio value, an insulin sensitivity value, and a snack size value; such parameters can be impacted by the time of day. The parameter values may be provided by a user such as the patient or a treating physician of the patient. The parameter values can be uploaded by a configuration device or provided via the touch display 16 of the device 10. The parameter values are utilized by the bolus calculator 22a to determine bolus recommendations for the patient.

Figure 3A:
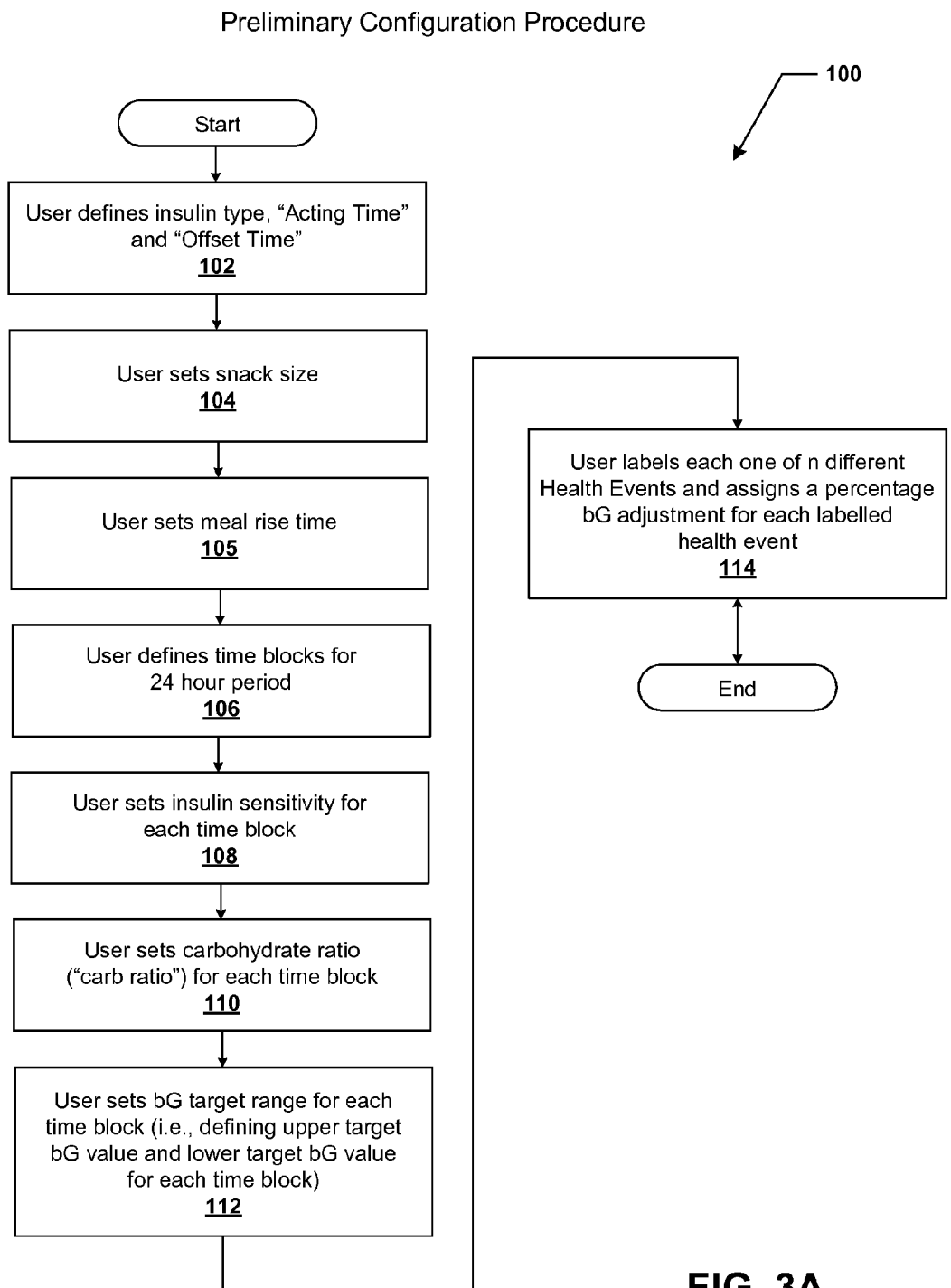
FIG. 3A is an exemplary flowchart illustrating a preliminary configuration procedure for configuring the bolus calculator module of the device shown in FIG. 1.

Referring to FIG. 3A, a flowchart 100 illustrates an exemplary preliminary configuration procedure that the user can perform to configure the various inputs needed to tailor the device 10 to the requirements of the user. At operation 102 the user can define the insulin type that she/he is using, as well as the "acting time" and "offset time" associated with the specified insulin. The user also sets a snack size at operation 104. Any carbohydrate amount greater than the snack size that the user enters into the device 10 will be considered as a "meal" by the device 10. A meal rise glucose amplitude (expressed in bG units) is also defined by the user at operation 105. At operation 106 the user can define the various time blocks for a twenty four hour period. In one exemplary implementation the user may define up to eight contiguous time blocks during a twenty four hour period. However, it will be appreciated that a greater or lesser number of time blocks could be provided for. Since the user's insulin sensitivity will be assumed to vary over the course of the day, the user can set a different insulin sensitivity value for each time block, as indicated at operation 108. At operation 110 the user can set a carbohydrate ratio ("carb ratio") for each time block as well, as this ratio can be assumed to vary for different users throughout the course of a day. At operation 112 the user can set a bG target range for each time block, as this range is also presumed to vary slightly over the course of a day. The bG target range is made up of an upper target bG value and a lower target bG value which define the upper and lower bounds, respectively, of the bG target range. It will also be appreciated that the processing subsystem 22 operates to consider an action shape of a previously taken correction bolus, where the action shape is defined by a bG lowering potential of the previously taken correction bolus, as well as the offset time and the acting time of the insulin associated with the previously taken correction bolus. The action shape is considered by the processing subsystem 22 when generating a new bolus recommendation, and will be discussed in greater detail below.

At operation 114 the user labels each one of up to n different health events with a label using the touchscreen display 16 and assigns a percentage bG adjustment for each labeled health event. It is a valuable feature of the device 10 that the user is able to program these various percentage adjustments for each of a plurality of user defined health events that the user knows in advance will affect her/his bG test values. For example, the user may program the device with different bG percentage adjustment values for health events such as "exercise", "illness", "stress", or even for recurring conditions such as a menstrual cycle. The precise percentages selected by the user for each user defined health event can be based on past history and experience of the user or based in part on the advice of a health care professional who is helping the user to manage her/his blood glucose levels. As one example, if the user knows from experience that an exercise event performed right after a meal will reduce a needed meal bolus by about 20%, then the user may enter "−20" in a displayed field on the display 16. The processing subsystem 22 will thereafter use this 20% reduction in calculating the meal bolus and the correction bolus when the exercise event has been selected. These features will be defined in greater detail in the following paragraphs.

Figure 3B:
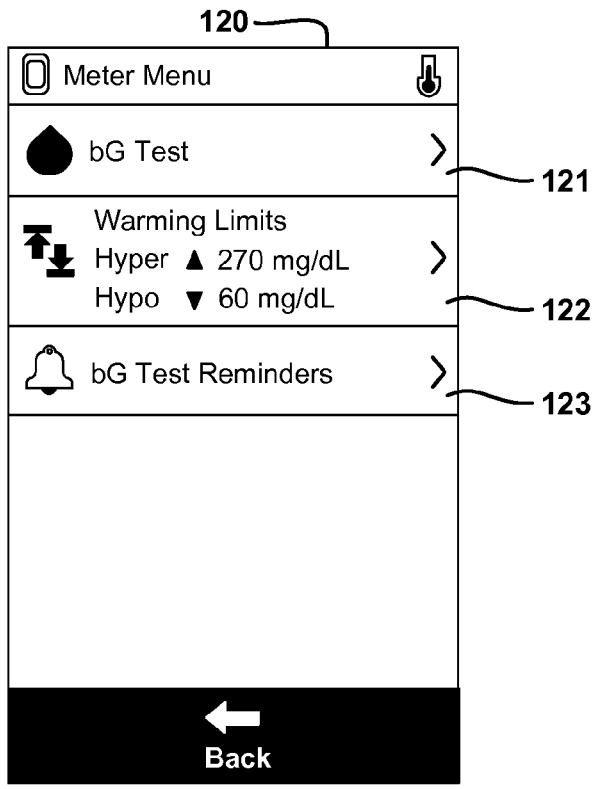
Figure 3C:
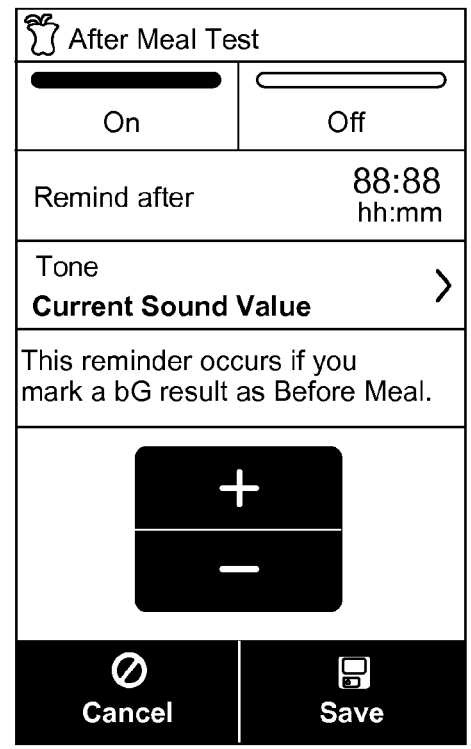

FIGS. 3B-3E illustrate an exemplary graphical user interface associated with the diabetes management device 10. From a main menu, the user may select a meter menu to perform functions associated with taking a blood glucose measure. An exemplary meter menu 120 is shown in FIG. 3B. Selections available on the meter menu may include conducting a blood glucose test 121, configuring warning limits 122, or setting test reminders 123. The diabetes management device 10 may be pre-configured with different types of test reminders. Pre-configured test reminders may include an after meal test reminder, an after high blood glucose measure reminder and an after low blood glucose measure reminder. Exemplary user interfaces for these test reminders are shown in FIGS. 3C-3E, respectively. It is also envisioned that the diabetes management device 10 can support user defined test reminders.

Figure 3F:
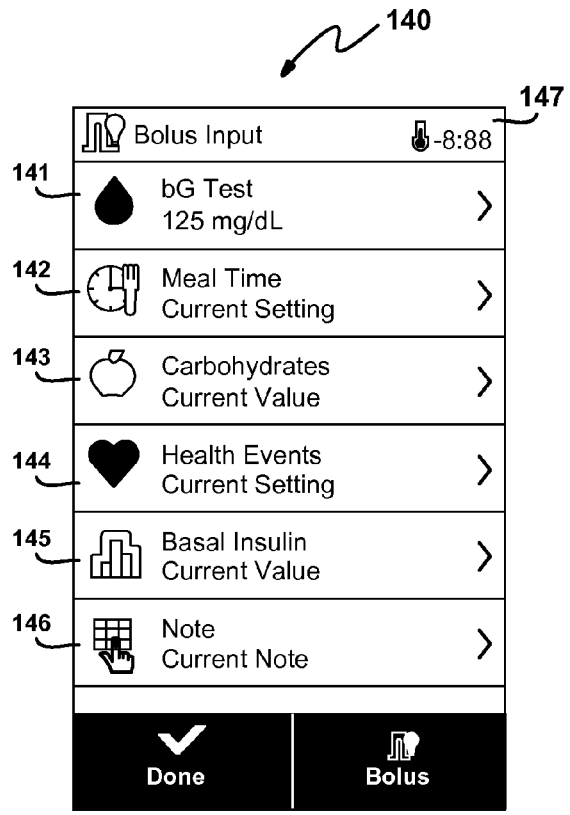
FIG. 3F depicts an exemplary graphical user interface presenting user configured inputs to the bolus calculator.

Following a meal or in connection with other types of health events, the user may seek bolus recommendation or bolus advice. Upon requesting bolus advice, the user is presented with a Bolus Input screen 140 as shown in FIG. 3F. The Bolus Input screen 140 presents a listing of items which may serve as input to the bolus calculator. Exemplary items may include but are not limited to a blood glucose measure 141, meal time indicator 142, carbohydrate value 143, health event selections 144, basal insulin amount 145, and a user provided note 146. Selection of an item navigates to another screen which enables the user to input the item.

Figure 3G:
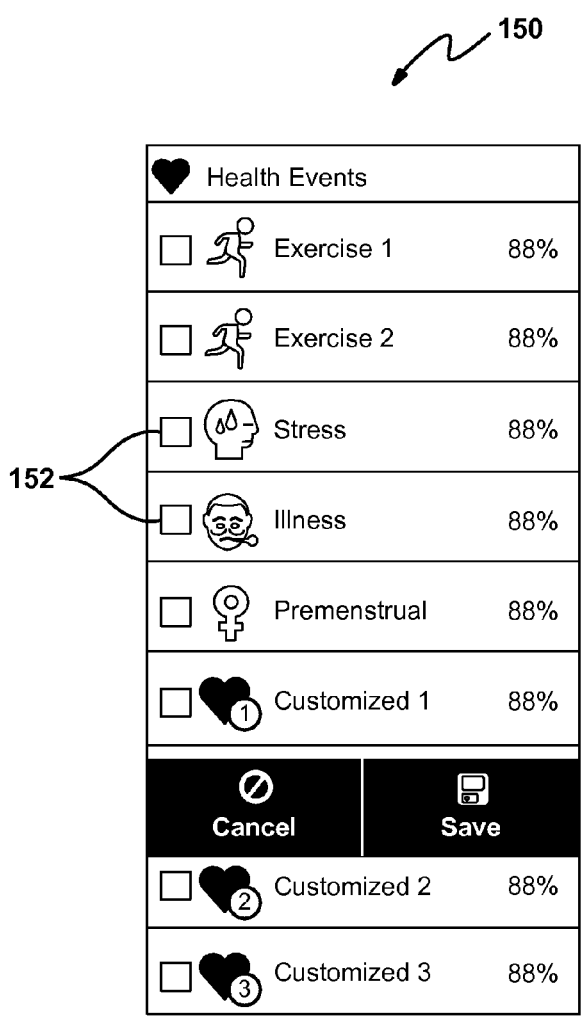
FIG. 3G depicts an exemplary graphical user interface that enables a user to select specific health events to associate with an insulin recommendation.

FIG. 3G illustrates a Health Event Selection screen 150 that enables the user to select specific health events to associate with an insulin recommendation. In an exemplary embodiment, different types of health events are presented for selection by the user. The user can select one of the boxes 152, which will mark just-obtained bG test value with the user programmed specific health event. The user can also adjust the percentage adjustment associated with each specific health event. When an insulin recommendation is requested or otherwise computed, the value of the insulin recommendation is adjusted in accordance with the specified adjustment percentage.

Figure 3H:
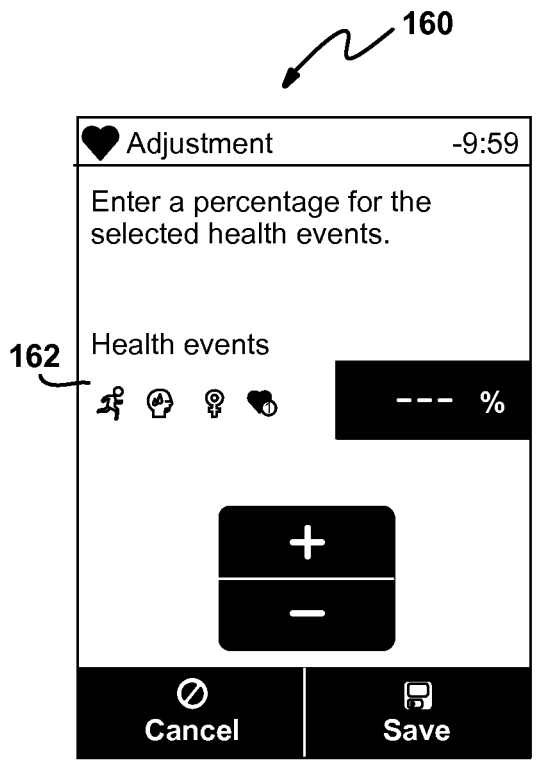
FIG. 3H depicts an exemplary graphical user interface that enables a user to enter a percentage that signifies a cumulative effect of the associated health events on the insulin recommendation for the patient.

In some instances, the user may associate more than one health event with a blood glucose measure. When a request is made for an insulin recommendation, the bolus calculator first determines how many events are associated with the blood glucose measure. If more than one health event is associated with the blood glucose measure, the user is prompted for further input. In one embodiment, the user is presented with a Health Event Adjustment screen 160 as shown in FIG. 3H. Of note, an icon for each associated health event is displayed on the Health Event Adjustment screen as indicated at 162. Rather than adjust an insulin recommendation individually for each health event, the user specifies a percentage that signifies a cumulative effect of the associated health events on the insulin of the patient. The value of the insulin recommendation is then adjusted in accordance with the designated percentage. An exemplary computation of an insulin recommendation is further described below.

Figure 3I:
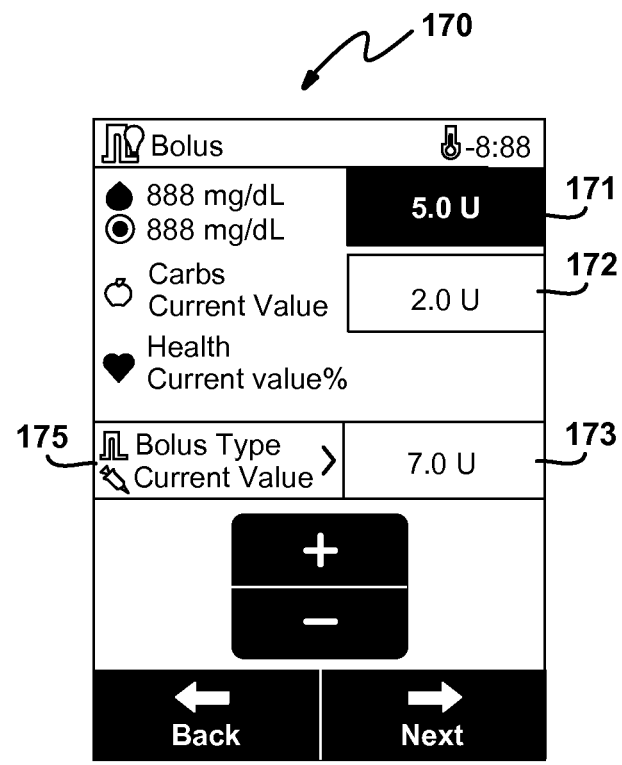
FIG. 3I depicts an exemplary graphical user interface that presents an insulin recommendation to the user.
Figure 3J:
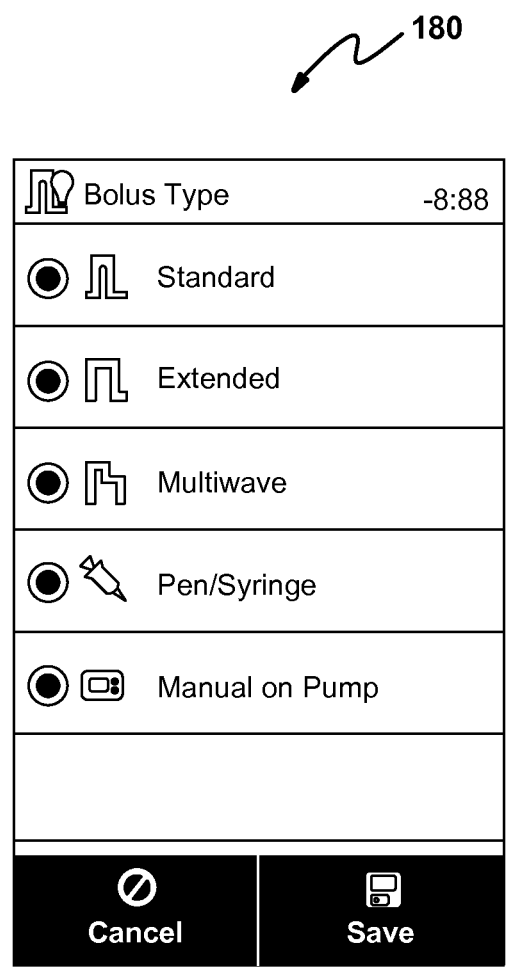
FIG. 3J depicts an exemplary graphical user interface that enables a user to specify the type of bolus to be administered.

Before proceeding with insulin administration, the insulin recommendation is presented to the user as shown in FIG. 3I. More specifically, the insulin recommendation is comprised of three components: a correction amount 171, a meal amount 172 and a total amount 173 of insulin. As further explained below, the correction amount 171 is intended to lower a patient's blood glucose level to a target value; whereas, the meal amount 172 is intended to compensate for carbohydrates consumed by the patient. The total amount 173 is equal to the sum of the correction amount and the meal amount. The recommended amounts may be adjusted by the user. In addition, the user may select how the bolus insulin is to be delivered as indicated at 175. Selection of the bolus type navigates the user to a Bolus Type Selection screen 180 as shown in FIG. 3J. Additional functionality associated with the bolus advice screens is further described below in relation to FIGS. 14-17.

Figure 4A:
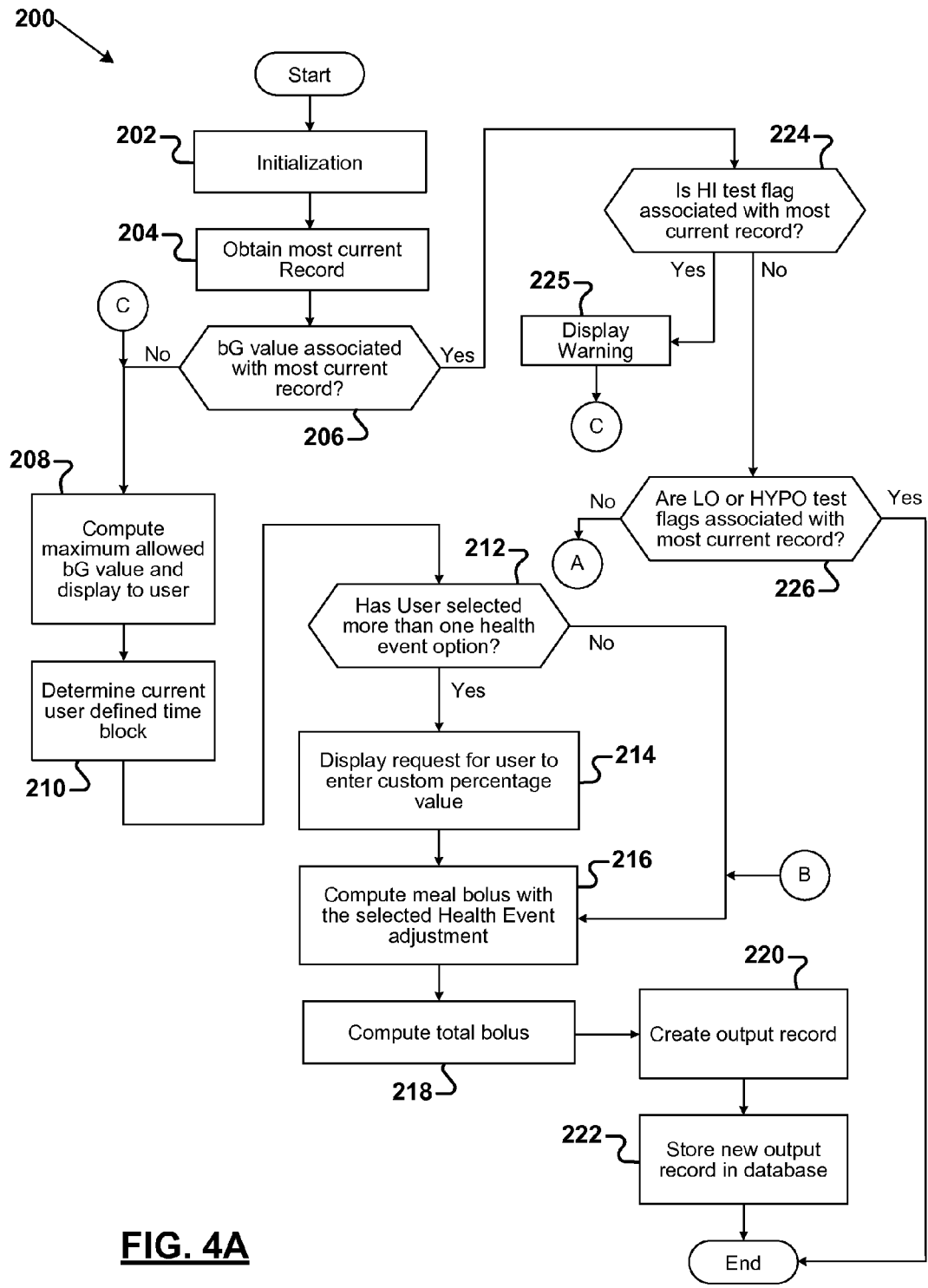
FIGS. 4A and 4B represent an exemplary flowchart illustrating operations that can be performed in computing a total bolus using user defined health adjustment percentages by which the computed meal bolus and computed correction bolus can be modified (by the user) before calculating a recommended total bolus.
Figure 4B:
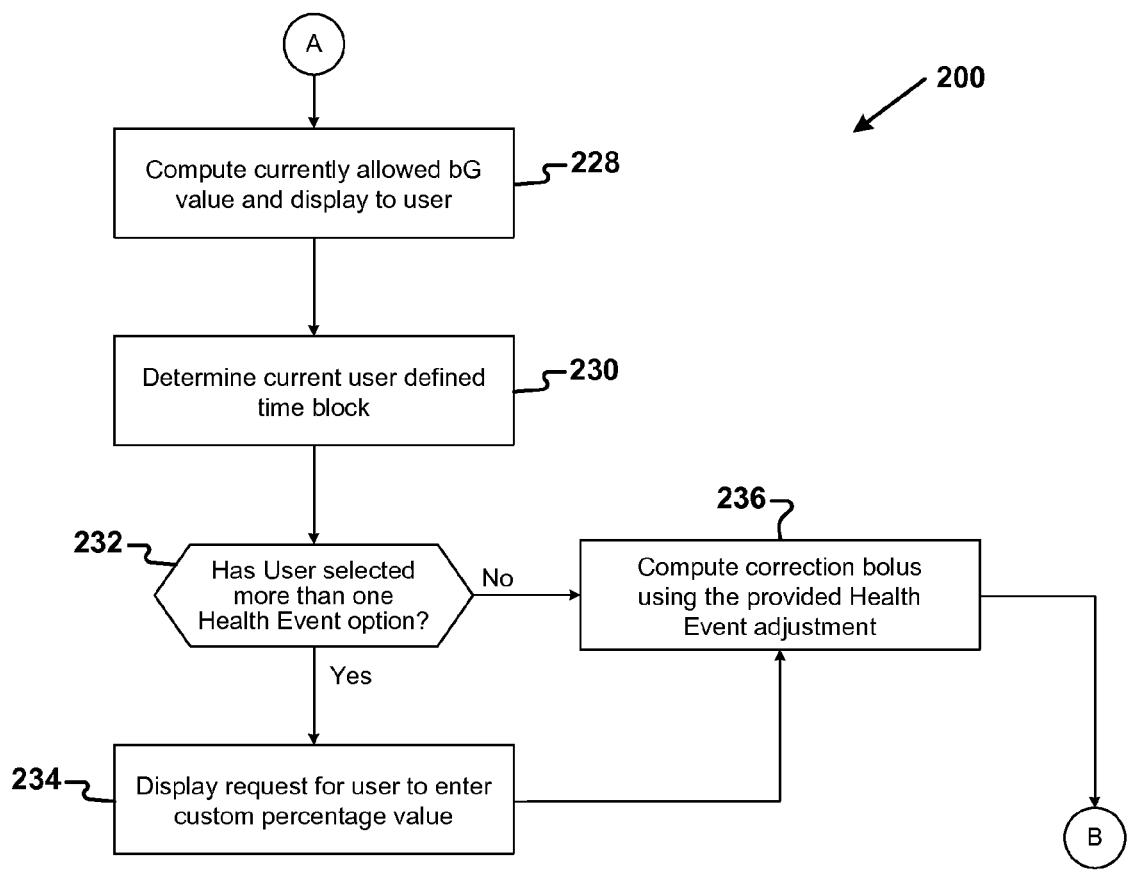

Referring now to FIGS. 4A and 4B, a flowchart 200 is shown of exemplary operations that can be performed by the device 10 in determining a total bolus recommendation for the user that takes into account the configuration programmed into the device 10 by the user. At operation 202 an initialization operation is performed to set the record contents of the processing subsystem 22 to "0". At operation 204 the processing subsystem 22 obtains the most current record stored in the database 26 and checks at operation 206 to determine if it has an associated bG test value. If not, then at operation 208 the maximum allowed bG value is computed and displayed to the user. At operation 210 the processing subsystem 22 determines the current time block. At operation 212 the processing subsystem 22 checks to determine if the user has selected more than one health event option and, if the user has selected more than one option, a request is made on the display 16 for the user to enter a custom percentage value, as indicated at operation 214, that will be applied to subsequent meal bolus and correction bolus calculations. At operation 216 the processing subsystem 22 will compute the meal bolus and apply the selected health event adjustment defined by the user (if any such adjustment has been selected by the user). At operation 218 the processing subsystem 22 will compute the total bolus. At operation 220 the processing subsystem 22 will update and store the output along with the record in the database 26 at operation 222.

Referring further to FIGS. 4A and 4B, if the check at operation 206 reveals that there is a bG value associated with the most current record, then a check is made at operation 224 to see if the "HI" test flag of the record is set, indicating a bG reading that is above a display limit of the device 10, and which therefore will not be used to calculate a recommended correction bolus. If this check provides a "Yes" answer, then after the display of an appropriate warning at operation 225 for a HI bG reading, operations 208-222 may be performed to obtain only a recommendation for a meal bolus. If the check at operation 224 produces a "No" answer, then a check is made to determine if the "LO" or "HYPO" test flags are set for the most current record (Advice Record_IN), as indicated at operation 226. This is an extra check to prevent the recommendation of a bolus in either a hypoglycemic condition or with a bG reading below the display limit of the device 10. In the event of a "Yes" answer, the routine of flowchart 200 ends (and flowchart 300 shown in FIG. 5 begins for calculating a carbohydrate suggestion). If the check at operation 226 produces a "No" answer, then at operation 228 in FIG. 4B the processing subsystem 22 computes the maximum allowed bG value and displays it to the user on the display 16.

Continuing in FIG. 4B, at operation 230 the processing subsystem 22 determines the current user defined time block. At operation 232 the processing subsystem 22 checks to determine if the user has selected more than one health event option and, if the user has selected more than one option, a request is made on the display 16 for the user to enter a custom percentage value, as indicated at operation 234, that will be applied to the correction bolus calculation at operation 236. At operation 236 the processing subsystem 22 will compute the correction bolus and apply the selected health event adjustment defined by the user (if any such adjustment has been selected by the user). Operations 216-222 from FIG. 4A will then be applied. If the check at operation 232 produces a "No" answer, the operation 236 will be performed using the user set health event adjustment.

Figure 5:
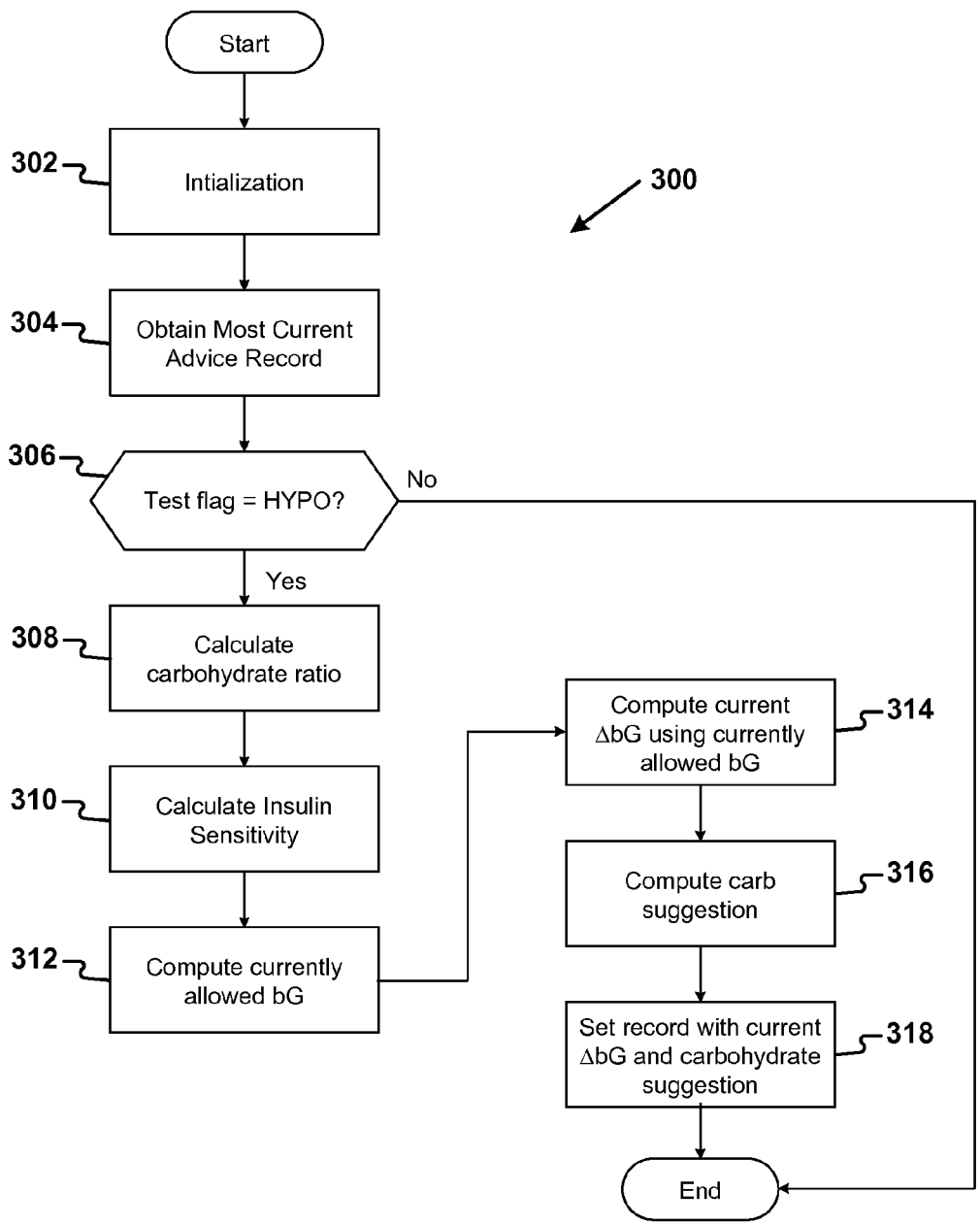
FIG. 5 is an exemplary flowchart illustrating operations that can be performed by the device of FIG. 1 in calculating a carbohydrate suggestion for the user.

Turning to FIG. 5, a flowchart 300 is shown illustrating exemplary operations to show a carbohydrate suggestion can be calculated using the device 10 (this flow occurs based on the "Yes" path at operation 226 in FIG. 4A). At operation 302 an initialization procedure is performed to ensure that any pre-existing data that may be present in the output contents of the processing subsystem 22 is cleared. The most current record is then obtained at operation 304. At operation 306 a check is made to determine if the HYPO test flag of the most current record is set, indicating a hypoglycemic condition for the current bG test value being analyzed. If so, the processing subsystem 22 computes the carbohydrate ("carb") ratio at operation 308 in the traditional manner. At operation 310 the insulin sensitivity is calculated in the traditional manner. At operation 312 the currently allowed bG is computed, which is described in greater detail below. At operation 314 the current delta bG is computed by subtracting the currently allowed bG from the most current record bG concentration. So in effect, operation 314 allows a previously taken correction bolus, which would operate to lower the user's bG, to be factored into the equation for determining the current delta bG. At operation 316 the current delta bG is converted into a carbohydrate suggestion using the insulin sensitivity and by the carbohydrate ratio factors. At operation 318 the outputs of carbohydrate suggestion and current delta bG are stored. The carbohydrate suggestion may be subsequently provided to the user as part of a bolus recommendation. Furthermore, the carbohydrate suggestion value may be used as a default value on an interface that captures a user input for the amount of carbs consumed.

Figure 6:
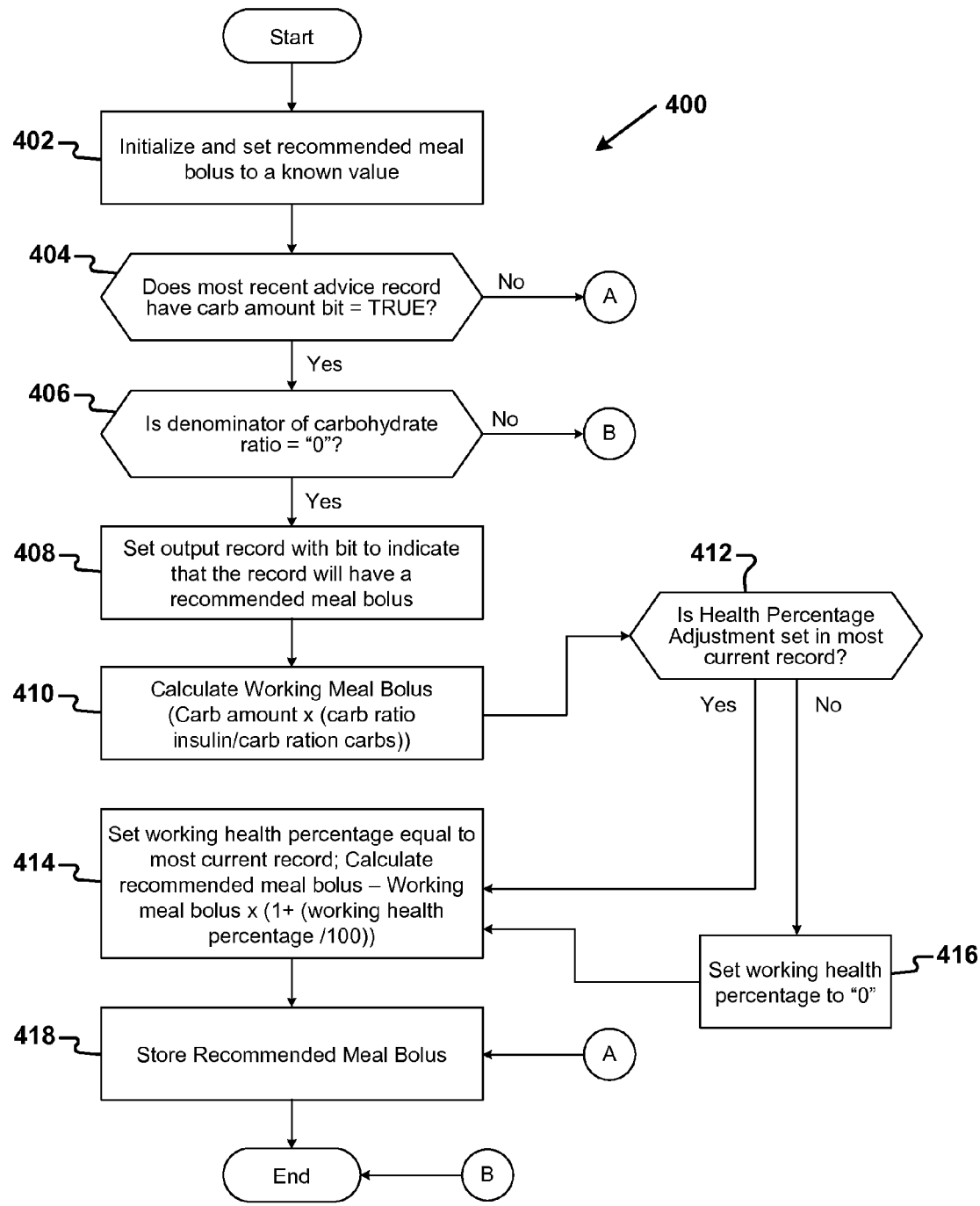
FIG. 6 is a flowchart illustrating exemplary operation performed by the device of FIG. 1 in computing the recommended meal bolus with a user programmed health adjustment applied thereto.

Referring now to FIG. 6, a flowchart 400 is shown illustrating one exemplary manner of computing a meal bolus with a health event adjustment (this flow is called out at operation 216 of FIG. 4B). At operation 402 an initialization is performed to set the recommended meal bolus to a known value. At operation 404 a check is made to determine if the most current record retrieved by the processing subsystem 22 from the database 26 has a carbohydrate amount available for use in the following calculations. A time out may be used to limit the amount of time that the carb value is available for use. If the answer is "Yes", then at operation 406 a check is made to ensure that the denominator of the carbohydrate ratio is not "0". If it is not, then at operation 408 a bit will be set for the output being created by the processing subsystem 22 to indicate a recommended meal bolus is associated with it. At operation 410 the working meal bolus is calculated. At operation 412 a check is made if a health event adjustment percentage is set in the most current record. If so, then at operation 414 a working health percentage is set equal to the health percentage contained in the most current record, and the recommended meal bolus is calculated at operation 414 using this working health percentage. For example, if the user has indicated "-20" in her/his percentage adjustment for the associated health event, then operation 414 uses this information to convert the "-20" to 80%, and the 80% figure is used to modify the working meal bolus to come up with the recommended meal bolus. Thus, in this example the recommended meal bolus would be reduced by 20%. At operation 418 the recommended meal bolus output just created by the processing subsystem 22 is saved in the log records portion 26a of the database 26.

If the check at operation 412 indicates that no health percentage adjustment is indicated in the most current record, then the working health adjustment percentage is set equal to zero at operation 416 and then operations 414 and 418 are repeated. If in operation 404 it is understood that there is no carbohydrate amount from which a recommended meal bolus can be calculated, the recommended meal bolus of zero is simply saved at operation 418. If the denominator of the carbohydrate ratio of the most current record is found to be "0" at operation 406, then the routine ends with an error condition.

Figure 7:
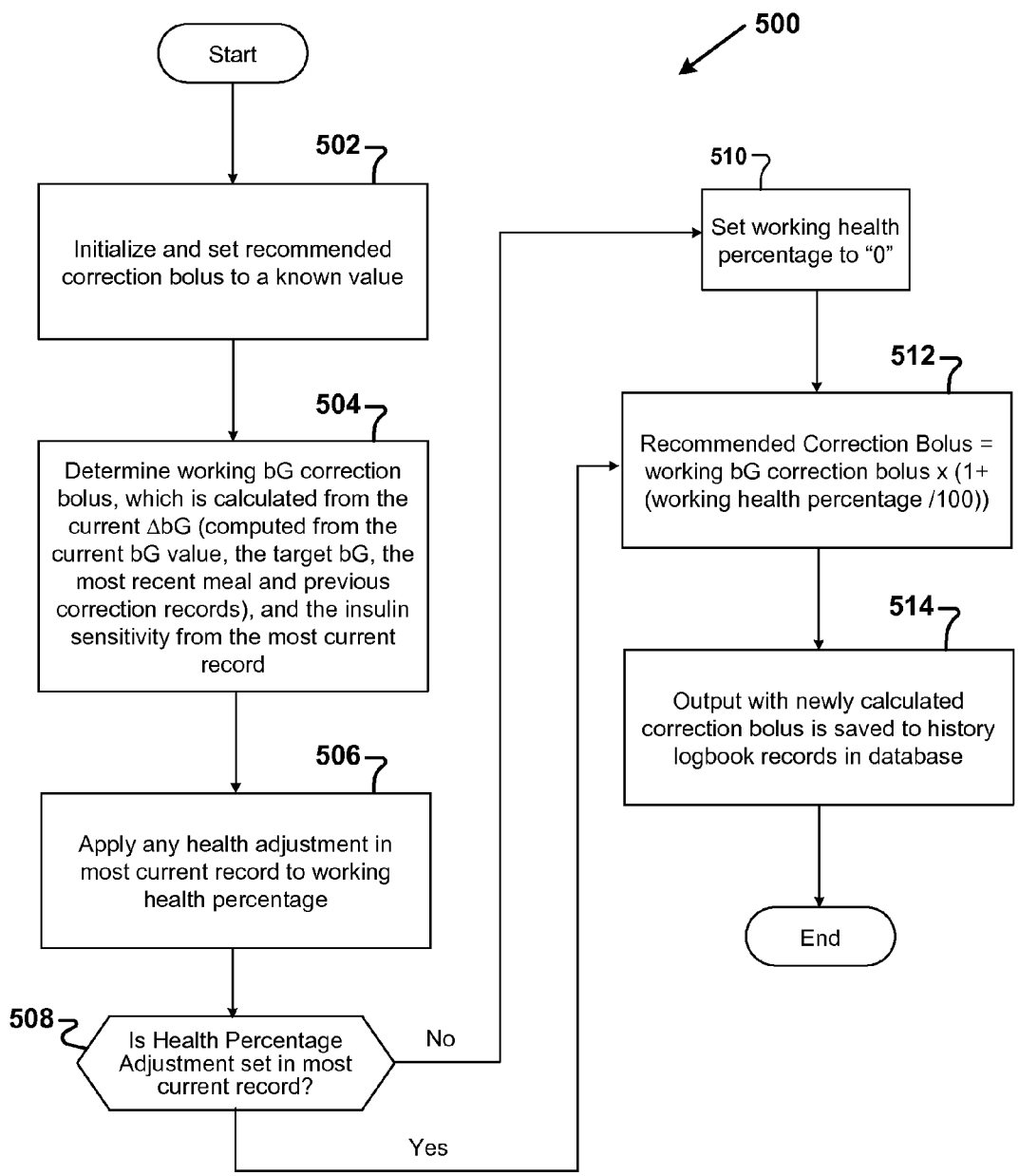
FIG. 7 is a flowchart illustrating exemplary operations that can be performed in computing a recommended correction bolus with a health adjustment percentage set by the user.

Referring to FIG. 7, there is shown an exemplary flowchart 500 setting forth operations that can be performed in computing a correction bolus, taking into account a percentage health adjustment input by the user. It will be appreciated that the operations of flowchart 500 are called by operation 236 in FIG. 4B.

At operation 502 the recommended correction bolus is initialized to a known value. At operation 504 the working bG correction bolus is calculated from the current delta bG (computed from the current bG value, the target bG, the most recent meal and/or previous correction records), and the insulin sensitivity from the most current record. At operation 506 any health adjustment percentage present in the most current record is applied to the working health percentage. Again, if the user has specified "None" when selecting a health adjustment percentage for the bG test value associated with the most current record, then the working health percentage will not be modified by any percentage value. At operation 508 the recommended correction bolus is obtained by modifying the working bG correction bolus by the health percentage adjustment. Thus, if the user had set the health adjustment percentage for the bG test value associated with the most current record to "−25", then the calculation at operation 508 would multiply the working bG correction bolus by 75%. The output with the newly calculated recommended correction bolus is then saved to the database history logbook records 26a at operation 510.

In calculating the correction delta bG, an advantage of the device 10 is that the working delta bG is allowed to be a negative value. This allows a portion of any correction to be removed from the newly calculated correction delta bG, such as if the user had previously taken some carbohydrates to compensate for a LO or HYPO bG value, to be factored into the newly calculated correction delta bG. Another advantage is that for computing a carbohydrate suggestion for the user, the recommendations can be calculated to the currently allowed bG value rather than to the center of the bG target range.

Figure 8:
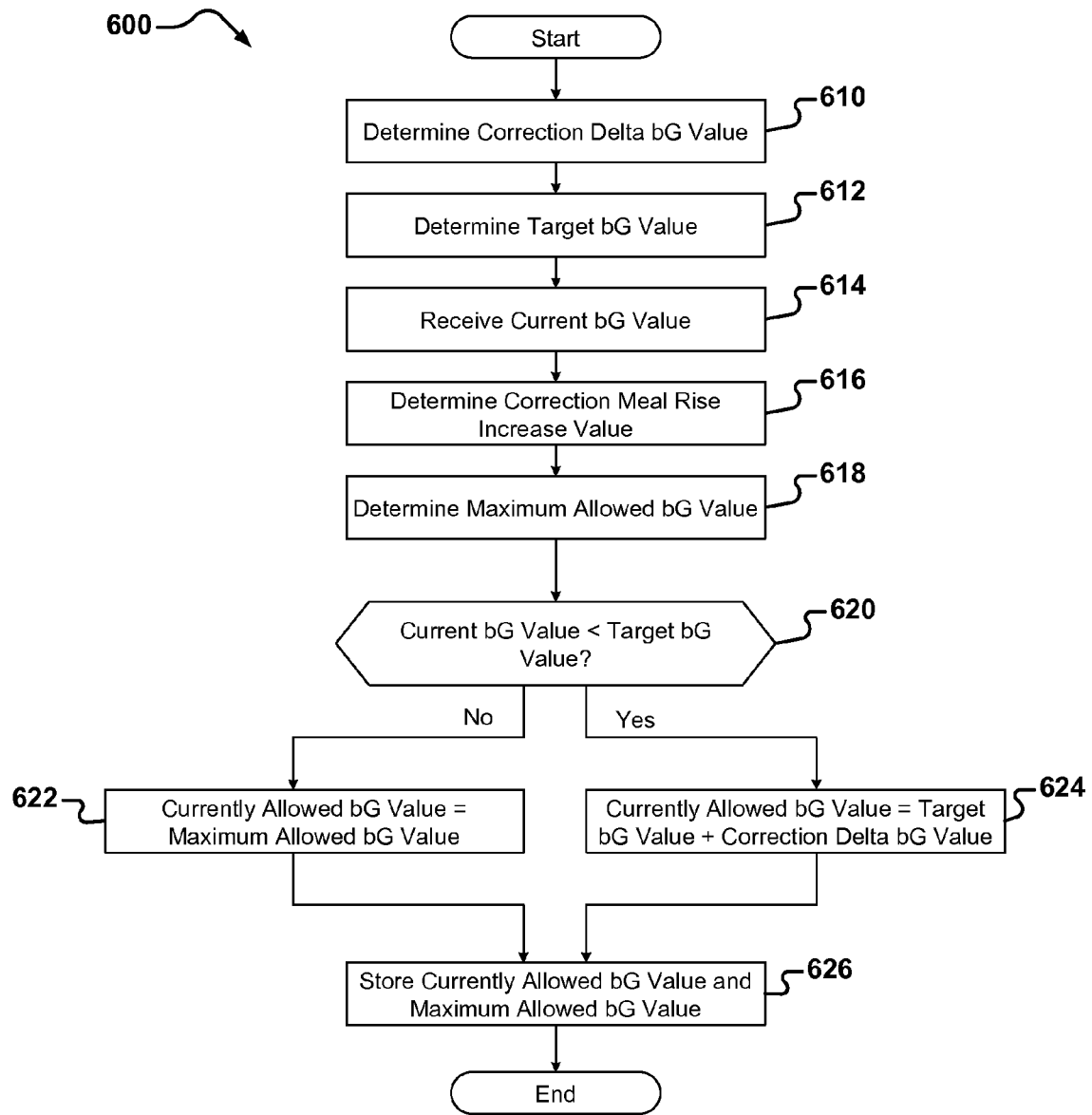
FIG. 8 is a flowchart illustrating exemplary operations that can be performed by the device of FIG. 1 in computing a currently allowed bG value.

As was discussed with respect to FIG. 5, a currently allowed bG value is computed at operation 312. Similarly, a currently allowed bG value is computed at operation 504 of FIG. 7. In some embodiments, the bolus calculator 22a computes the currently allowed bG value based on whether the current bG measurement of the patient is less than the target bG value of the patient. FIG. 8 illustrates an example method 600 for computing the currently allowed bG value. The currently allowed bG value is indicative of a value that a patient's bG value may increase to at a current time without requiring correction bolus. As should be appreciated the method 600 may be executed by the processing subsystem 22 of the device 10 and in particular, can be implemented as part of the bolus calculator 22a. For purposes of explanation, the method 600 is explained as being performed by the bolus calculator 22a.

At operation 610, the bolus calculator 22a computes a correction delta bG value. The correction delta bG value is indicative of an aggregated bG lowering effect of the events defined in the one or more active advice history records of the patient. An example method for determining the correction delta bG value is described in further detail below and with respect to FIG. 9.

At operation 612, the bolus calculator 22a computes a target bG value. In some embodiments, the target bG value is determined as an average of the upper target bG value and the lower target bG value. The upper target bG value and the lower target bG value can be provided to the device 10 by the patient or another user such as the treating physician. Further, the upper target bG value and lower target bG value may be stored in the advice history records. Alternatively, the target bG value can be manually entered by a user.

At operation 614, the bolus calculator 22a receives the current bG measurement value. As discussed above, the current bG measurement value can be determined when the patient provides a blood sample and the blood sample is analyzed by the device 10.

At operation 616, the bolus calculator 22a determines a correction meal rise value based on a specific advice history record of the plurality of advice history records. As will be discussed below, the specific advice history record that is used can include: i) an event corresponding to the patient eating a meal that is greater than a snack size, ii) an event corresponding to a meal bolus amount, and iii) an event corresponding to the patient or an insulin pump 36 verifying that insulin was actually administered to the patient. The correction meal rise value indicates an amount the bG level of the patient can increase as a result of a meal eaten by the patient and with respect to the target bG value without requiring an additional correction bolus. An example technique for determining the correction meal rise value is discussed in greater detail below and with respect to FIG. 10.

At operation 618, the bolus calculator 22a determines a maximum allowed bG value. The maximum allowed bG value indicates the maximum value for the patient's bG measurement before recommending a correction bolus to the patient. In some embodiments, the maximum bG value can be determined by summing the target bG value, the correction delta bG value, and the correction meal rise value.

At operation 620, the bolus calculator 22a compares the current bG measurement value with the target bG value. If the bolus calculator 22a determines that the current bG measurement value is greater than the target bG value, the bolus calculator sets the currently allowed bG value equal to the maximum allowed bG value, as shown at operation 622. If the bolus calculator 22a determines that the current bG measurement value is less than the target value, the bolus calculator 22a sets the currently allowed bG value equal to the sum of the target bG value and the correction delta bG value, as shown at operation 624. At operation 626, the bolus calculator 22a stores the currently allowed bG value and maximum allowed bG value.

It should be appreciated that the exemplary method 600 is provided for example only. Variations of the method 600 are contemplated and are within the scope of the disclosure. Further, the ordering of the operations are not intended to be limiting and different orderings are contemplated and within the scope of the disclosure.

Figure 9:
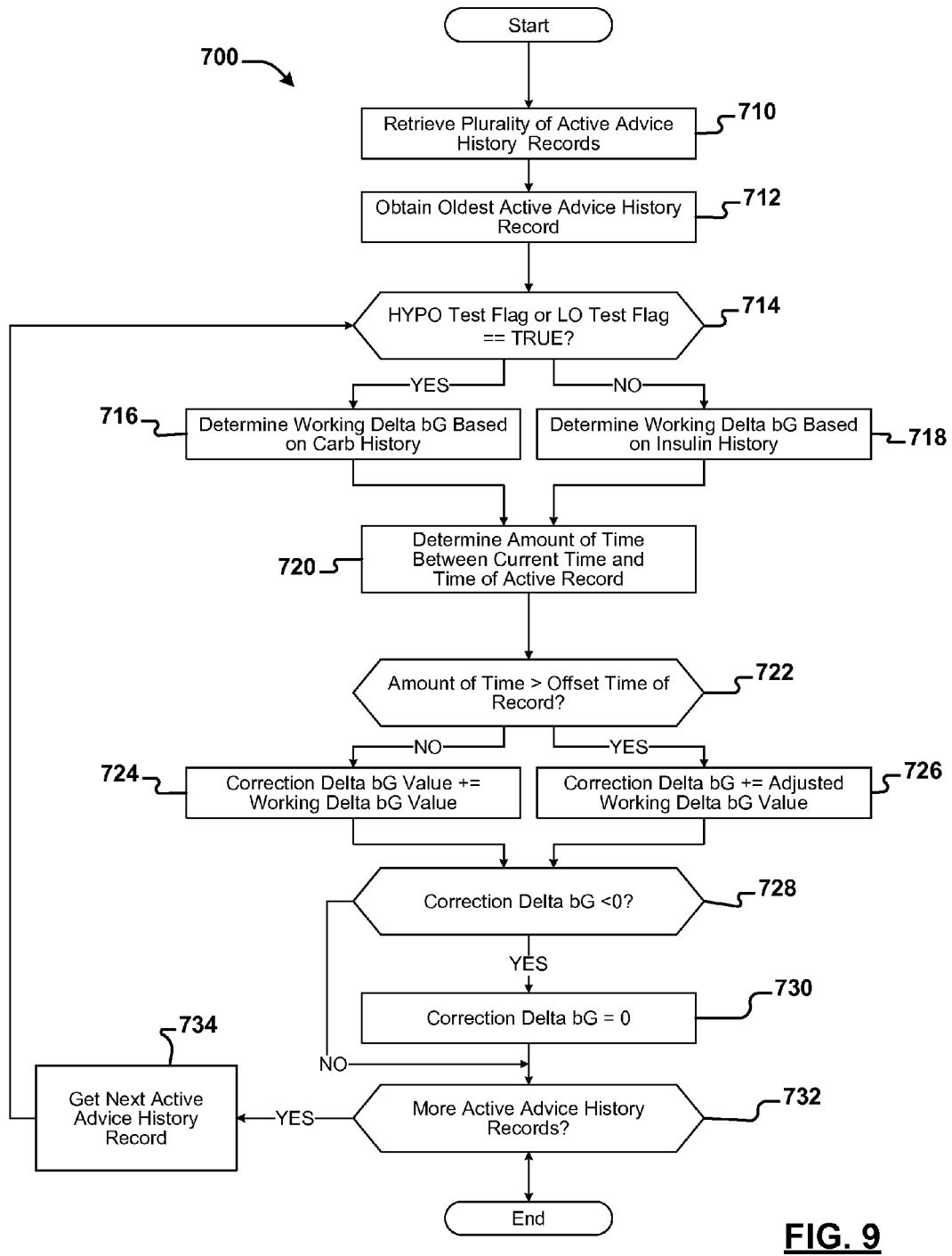
FIG. 9 is a flowchart illustrating exemplary operations that can be performed by the device of FIG. 1 in computing a correction delta bG value.

As was previously discussed, the bolus calculator 22a determines a correction delta bG value. The correction delta bG value indicates an aggregated bG lowering effect of the events defined in the advice history records. Put another way, the correction delta bG value indicates the overall lowering effect of the insulin that is still active in the patient's body. In some embodiments, the bolus calculator 22a analyzes the active advice history records from the oldest active advice history record to the most recent active advice history record to determine the aggregated bG lowering effect of the events defined therein. FIG. 9 illustrates an exemplary method 700 for determining the correction delta bG value. For purposes of explanation, the method 700 is described as being performed by the bolus calculator 22a.

At operation 710, the bolus calculator 22a retrieves the plurality of active advice history records. As previously described, the plurality of active advice history records are the advice history records defining events that are still affecting the patient's bG levels. For example, if an event defined in an advice history record is a correction bolus that was administered three hours prior to the current time and the active time of the insulin dose was three or more hours, the advice history record would be included in the plurality of active advice history records. Conversely, an advice history record corresponding to 48 hours prior to the current time, the advice history record would not be included in the plurality of active advice history records. At operation 712, the bolus calculator 22a selects the oldest advice history record of the plurality of active advice history records.

At operation 714, the bolus calculator 22a determines whether either of the HYPO test flag or the LO test flag in the selected advice history record is set to 1. If so, the bolus calculator 22a determines a working delta bG value based on a carbohydrate intake of the patient defined in the advice history record, as shown at operation 716. If neither the HYPO test flag or the LO test flag are set to 1 in the selected advice history record, the bolus calculator 22a determines the working delta bG value based on an insulin that was administered to the patient at a time corresponding to the selected active history record, as shown at operation 718. The working delta bG value is the amount by which the patient's bG level is currently decreased or increased by as a result of the events defined in the selected advice history record.

At operation 720, the bolus calculator 22a determines the amount of time that has lapsed since the selected advice history record was generated. As discussed, the advice history record includes a time corresponding to the advice history record. The bolus calculator 22a utilizes the time defined in the advice history record to determine the amount of time that has lapsed since the advice history record was generated.

At operation 722, the bolus calculator 22a determines whether the amount of time that has lapsed since the advice history record was generated is greater than the offset time defined in the advice history record. If the amount of time is less than the offset time, then the bolus calculator 22a increments the correction delta bG value by the full amount of the working delta bG value, as shown at operation 724. If the amount of time is greater than the offset time, the bolus calculator 22a increments the correction delta bG value by the result of a predetermined formula, as shown at operation 726. For example, in some embodiments the correction delta bG value is incremented by the amount:

$$\frac{WorkingDeltabG}{Acting\_Time - Offset\_Time} \times (Acting\_Time - Time)$$

Where Acting_Time is the duration during which events defined in the selected advice history record effects the bG level of a patient, Offset_Time is the duration during which the full effect of events defined in the selected advice history record apply, and Time is the difference between the current time and the time when the advice history record was generated. As should be appreciated, the differences in time, e.g., Acting_Time-Offset_Time and Acting_Time-Time may be represented in minutes or seconds. Furthermore, Acting_Time and Offset_Time may be defined in the selected active history record.

At operation 728, the bolus calculator 22a compares the running total of the correction delta bG value to a predetermined threshold, e.g., O. As should be appreciated, the bolus calculator 22a aggregates the total effect of bG influencing events defined in the plurality of active advice history records to calculate the correction delta bG. At each iteration, e.g., after analyzing another active advice history record, if the running total is less than 0, the bolus calculator 22a sets the running total for the correction delta bG to 0 at operation 730. Otherwise, the running total for the correction delta bG is not altered.

At operation 732, the bolus calculator 22a determines whether there are any remaining active advice history records remaining in the plurality of active advice history records left to analyze. If so, the bolus calculator 22a obtains the next advice history record, as shown at operation 734, and repeats the operations described above. Else, the bolus calculator 22a stops the routine and stores the aggregated correction delta bG value.

It is appreciated that the foregoing method 700 is provided for example only and not intended to be limiting. Other techniques for determining the correction delta bG value are contemplated and are within the scope of the disclosure.

Figure 10:
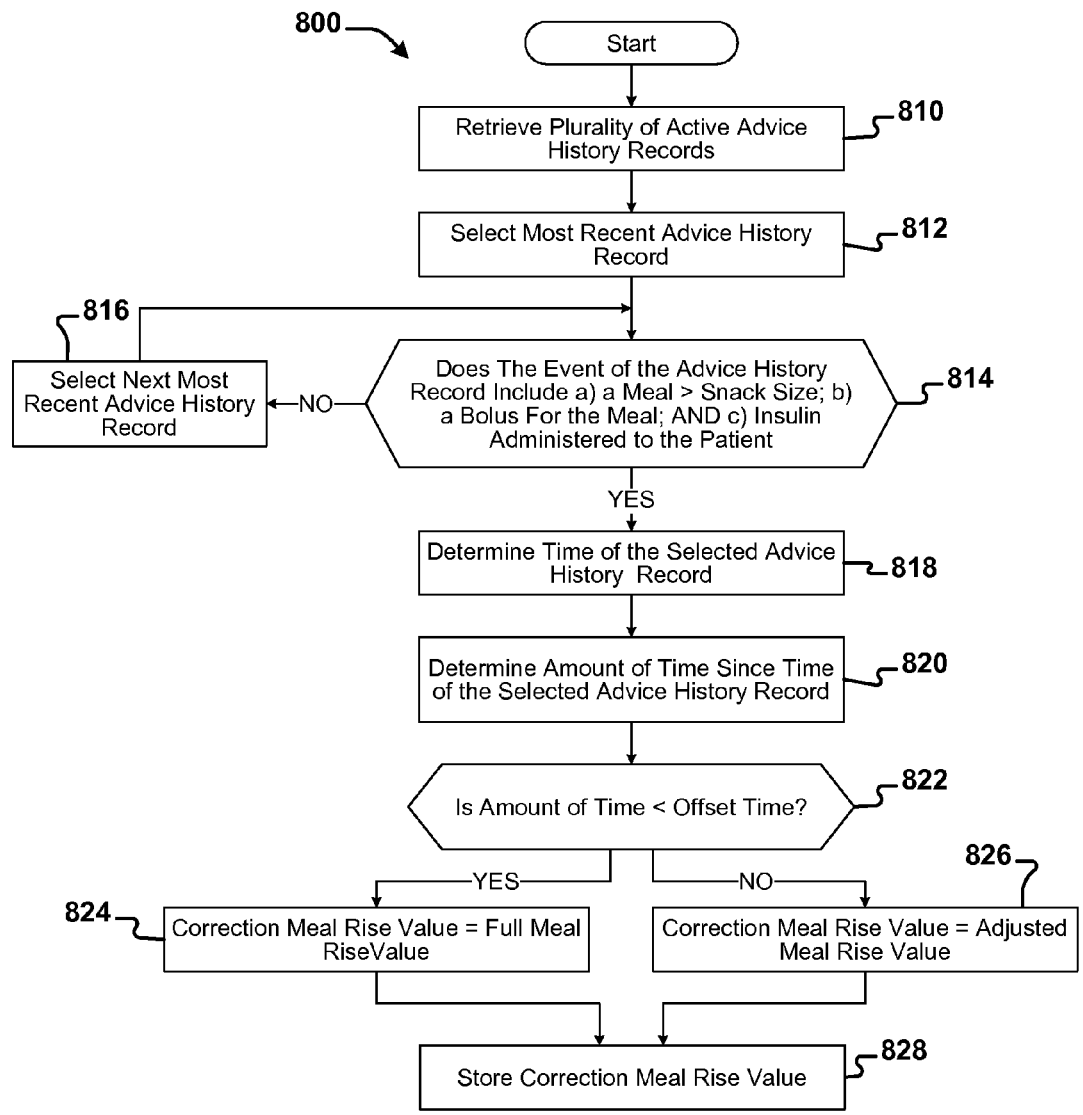
FIG. 10 is a flowchart illustrating exemplary operations that can be performed by the device of FIG. 1 in computing a correction meal rise value.

As described above, the bolus calculator 22a is configured to determine a correction meal rise value, which is indicative of an amount the bG level of the patient can increase with respect to the target bG value without requiring a meal bolus. In some embodiments, the bolus calculator 22a analyzes the active advice history records to select the most recent relevant active advice history record. Using the selected active advice history record, the bolus calculator 22a determines the amount of time that has lapsed since the record was generated to determine the correction meal rise value. FIG. 10 illustrates an example method 800 for determining a correction meal rise value. For purposes of explanation, the method 800 is explained as being executed by the bolus calculator 22a.

At operation 810, the bolus calculator 22a obtains the plurality of active advice history records. As described previously, the plurality of active advice history records are the advice history records that were generated within an acting time. That is, the events defined in the advice history record may be still influencing the bG measurements of a patient. At operation 812, the bolus calculator 22a selects the most recent advice history record.

At operation 814, the bolus calculator 22a analyzes the selected advice history record to determine whether the advice history record includes: i) an event corresponding to the patient eating a meal that is greater than a snack size, ii) an event corresponding to a meal bolus amount, and iii) an event corresponding to the patient or an insulin pump 36 verifying that insulin was actually administered to the patient.

If one or more of the conditions are not met, the bolus calculator 22a obtains the next most recent advice history record, as shown at operation 816. If all of the above-identified conditions are met, the bolus calculator 22a determines the time of the selected advice history record, as shown at operation 818. It is noted that if the bolus calculator 22a cannot identify a record meeting the above-stated criteria, the method ends and the meal rise value is set equal to 0.

At operation 820, the bolus calculator 22a determines the amount of time that has lapsed since the selected advice history record was generated. At operation 822, the bolus calculator 22a determines whether the amount of time that has lapsed is less than the offset time defined in the selected advice history record. If the amount of time is less than the offset time, the correction meal rise value is set equal to the full amount of the meal rise value, as indicated in the action shape defining meal rise values, as shown at operation 824. As discussed, the values of the action shape may be entered by a user such as the patient or a treating physician. If, however the amount of time is greater than the offset time, the bolus calculator 22a sets the correction meal rise value equal to an adjusted meal rise value, as shown at 826. In some embodiments, the bolus calculator 22a sets the correction meal rise value equal to the result of a predetermined formula, as shown at 826. For example, the adjusted meal rise value can be set equal to the result of the following formula:

$$\frac{Meal\_Rise}{Acting\_Time - Offset\_Time} \times (Acting\_Time - Time)$$

where Meal_Rise is the full meal rise value defined in the action shape corresponding to the selected advice history record, Acting_Time is the duration during which the selected advice history record effect the bG level of a patient, Offset_Time is the duration during which the full effect of the events defined in the selected advice history record apply, and Time is the amount of time since the selected advice history record was generated. Acting_Time and Offset_Time may be defined in the selected active history record. At operation 828, the correction meal rise value is stored.

It is appreciated that the foregoing method 800 is provided for example only and not intended to be limiting. Other techniques for determining the correction meal rise value are contemplated and are within the scope of the disclosure.

Figure 11A:
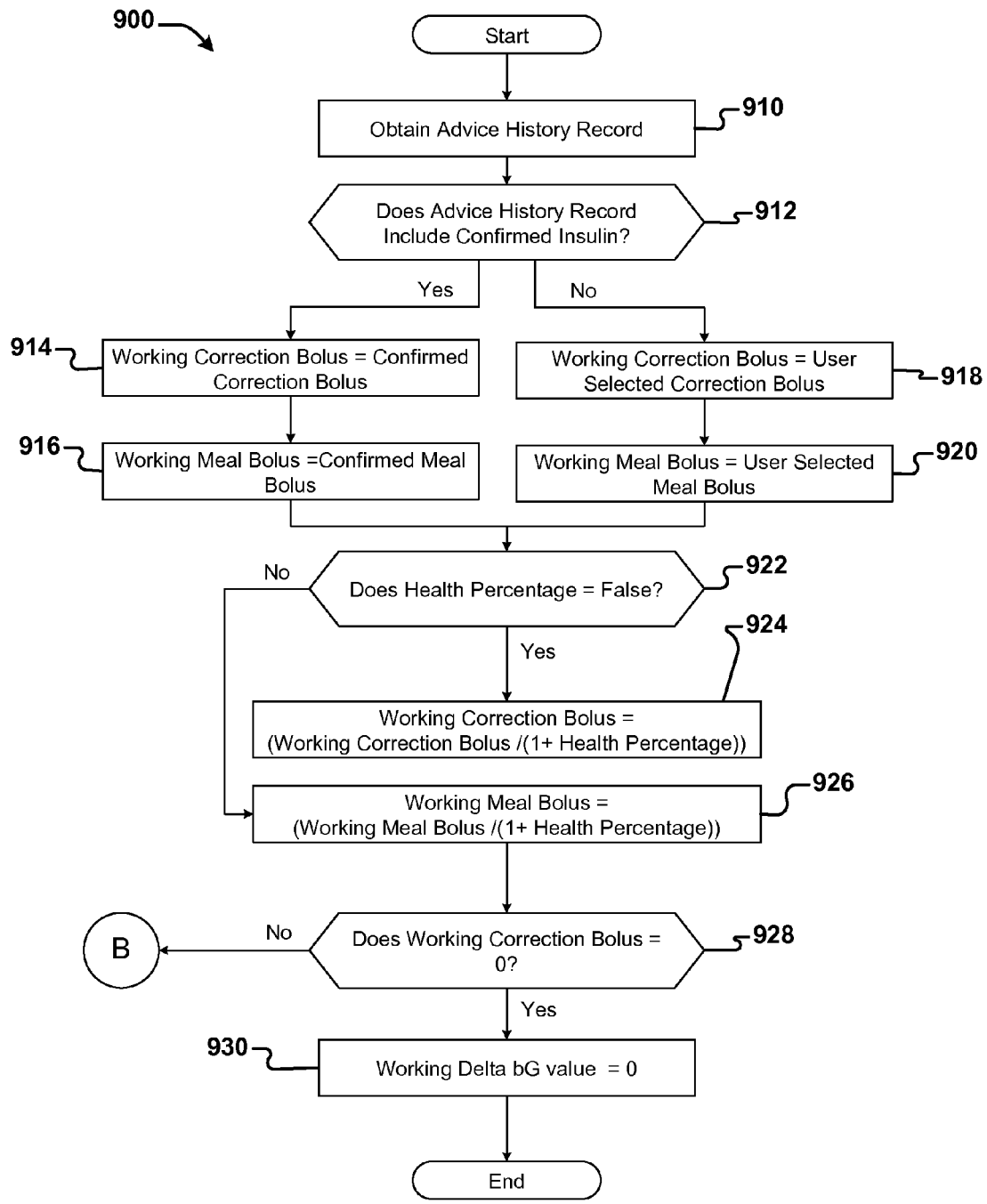
FIGS. 11A and 11B are flowcharts illustrating exemplary operations that can be performed by the device of FIG. 1 in computing a working delta bG value based on an insulin history of the patient.
Figure 11B:
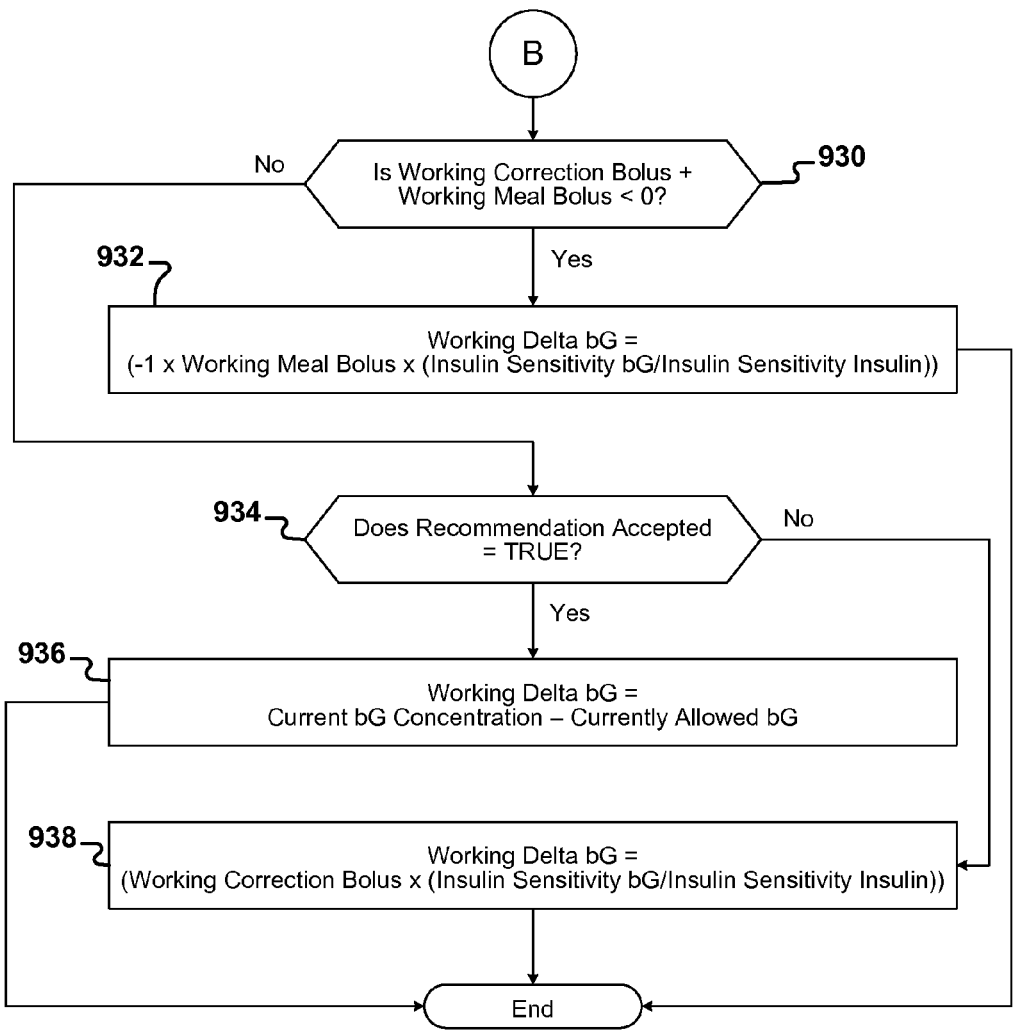

As previously discussed with respect to FIG. 9, when the bolus calculator 22a is determining the working correction delta bG value for a particular advice history record, the bolus calculator 22a determines whether the HYPO or LO test flag is set to true. If neither flag is set, the bolus calculator determines the working delta bG value based on the insulin history of the patient. FIGS. 11A and 11B together illustrate an example method 900 for determining the working delta bG value based on the insulin history the patient.

At operation 910, the bolus calculator 22a obtains the advice history record for which the working correction delta bG value is being calculated. At operation 912, the bolus calculator 22a determines whether the events defined in the advice history record include a confirmation that insulin was administered to the patient by an insulin pump 36. If so, a working correction bolus value is set equal to the confirmed correction bolus value identified in the advice history record and a working meal bolus value is set equal to the confirmed meal bolus value identified in the advice history record, as shown at operations 914 and 916, respectively. If there was no confirmed insulin defined in the advice history record, the bolus calculator 22a sets the working correction bolus value equal to the user selected correction bolus value identified in the advice history record and the working meal bolus value equal to the user selected meal bolus value, as shown at operations 918 and 920, respectively.

At operation 922, the bolus calculator 22a determines whether the health percentage value defined in the advice history record is defined. If a health percentage value is defined, the working correction bolus is set equal to:

$$\left(\frac{WorkingCorrectionBolus}{1 + HealthPercentage}\right)$$

where WorkingCorrectionBolus is the working correction bolus value as determined above and HealthPercentage is the health percentage value defined in the advice history record, as shown at operation 924. It is appreciated that the health percentage value can be a decimal representation of the percentage. Further, at operation 926, the working meal correction bolus value is set equal to:

$$\left(\frac{WorkingMealBolus}{1 + HealthPercentage}\right)$$

where WorkingMealBolus is the working correction bolus value determined above. It is appreciated that the health percentage value can be a decimal representation of the percentage. If at operation 922, a health percentage is not defined, the working correction bolus and the working meal bolus values are left unchanged.

At operation 928, the bolus calculator 22a determines whether the working correction bG value is equal to 0. If so, the bolus calculator 22a sets the working delta bG value equal to 0, as shown at operation 930, and the process returns the working delta bG value.

If the working correction bG value is not equal to 0, the bolus calculator 22a determines whether the sum of the working correction bolus value and the working meal bolus value is less than 0, as shown at operation 930. If so, the bolus calculator 22a, as shown at operation 932, calculates the working delta bG value according to:

$$Working\_Delta\_bG\_value = \\ -1 \times WorkingMealBolus \times \left(\frac{InsulinSensitivitybG}{InsulinSensitivityInsulin}\right)$$

where WorkingMealBolus is the working meal bolus value determined above, and InsulinSensitivitybG and InsulinSensitivityInsulin are predetermined values provided by the patient or another user in the advice history record. Once the working delta bG value is determined the method 900 ends.

If, however, the sum of the working correction bolus value and the working meal bolus value is not less than 0, the bolus calculator 22a determines whether the patient had accepted the bolus recommendation identified in the advice history record, as shown at operation 934. If so, at operation 936 the bolus calculator 22a determines the working delta bG value according to:

Working_Delta_bG_value=bG_Concentration−Currently_Allowed_bG where bG_Concentration is the measured bG concentration value identified in the advice history record and the Currently_Allowed_bG is the currently allowed bG value in the advice history record, the calculation of which was described in greater detail above. If the advice history record does not indicate that the bolus recommendation was accepted, at operation 938 the bolus calculator 22a determines the working delta bG value according to:

$$Working\_Delta\_bG\_value = \\ WorkingCorrectionBolus \times \left(\frac{InsulinSensitivitybG}{InsulinSensitivityInsulin}\right)$$

where WorkingCorrectionBolus is the working correction bolus value, described above, and InsulinSensitivitybG and InsulinSensitivityInsulin are predetermined values provided by the patient or another user in the advice history record. Once the working delta bG value is determined, the working delta bG value is returned and the method 900 stops executing.

It is appreciated that the foregoing method 900 is provided for example only and not intended to be limiting. Other techniques for determining the working delta bG value are contemplated and are within the scope of the disclosure.

Figure 12:
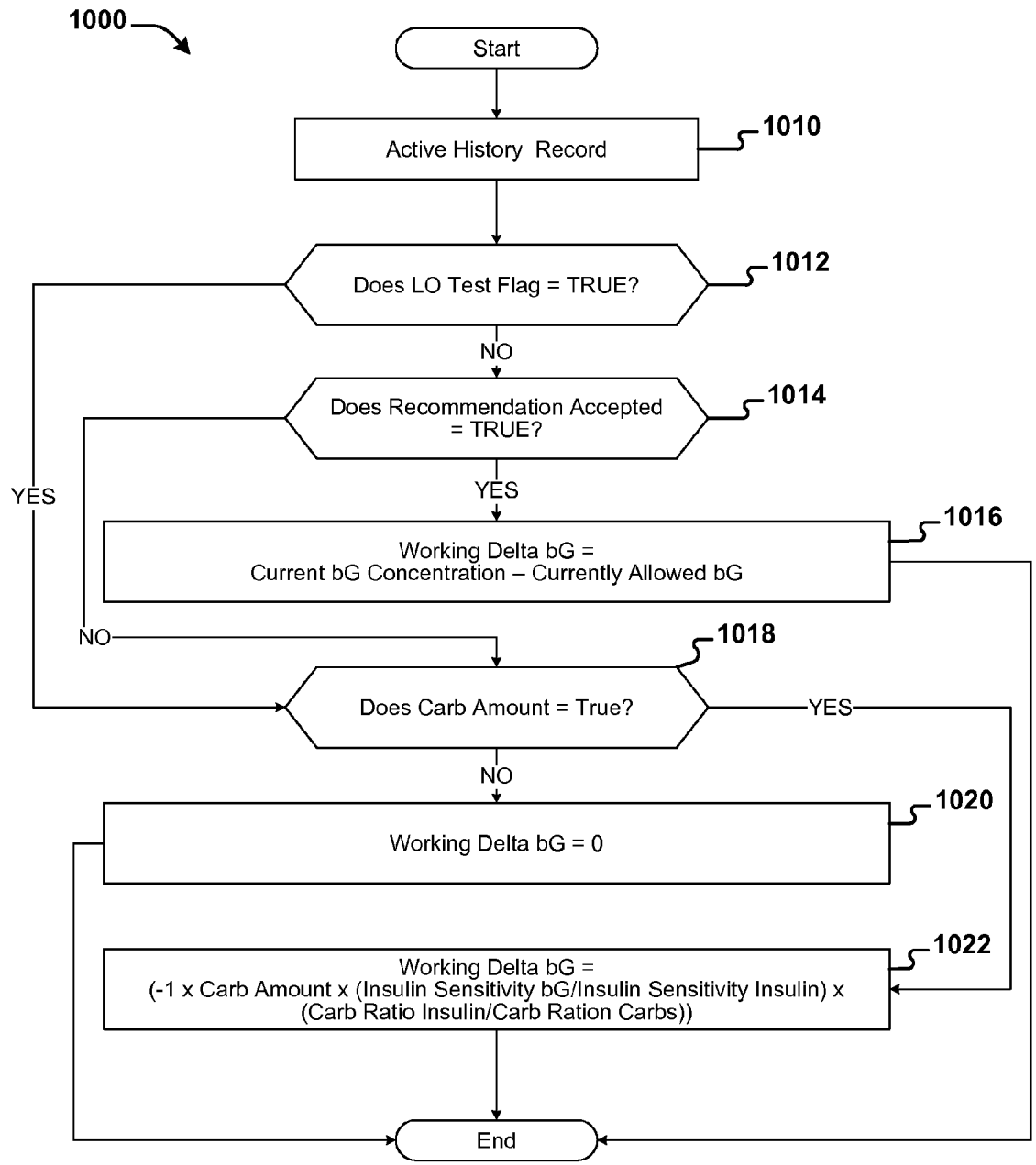
FIG. 12 is a flowchart illustrating exemplary operations that can be performed by the device of FIG. 1 in computing a working delta bG value based on a carbohydrate history of the patient.

As previously discussed with respect to FIG. 9, when the bolus calculator 22a is determining the working correction delta bG value for a particular advice history record, the bolus calculator 22a determines whether the HYPO or LO test flag is set to true. If one or both flags are set, the bolus calculator 22a determines the working delta bG value based on the carbohydrate history of the patient. FIG. 12 illustrates an example method 1000 for determining the working delta bG value based on the carbohydrate history the patient.

At operation 1010, the bolus calculator 22a receives the advice history record for which the working correction delta bG value is being calculated. At operation 1012, the bolus calculator 22a determines whether the LO test flag is set. If the LO test flag is not set, at operation 1014 the bolus calculator 22a determines whether the bolus recommendation indicated in the advice history record was accepted. If the bolus recommendation was accepted, at operation 1016 the bolus calculator 22a determines the working delta bG value according to the following:

$$Working\_Delta\_bG\_value = bG\_Concentration - Currently\_Allowed\_bG$$

where bG_Concentration is the measured bG concentration value identified in the advice history record and the Currently_Allowed_bG is the currently allowed bG value in the advice history record.

If the advice history record indicates that the LO test flag was true or the bolus recommendation was not accepted, the bolus calculator 22a determines whether a carbohydrate amount value as associated with the advice history record, as shown at operation 1018. If not, the working delta bG value is set equal to 0, as shown at operation 1020. If a carbohydrate value was associated with the advice history record, at operation 1022 the bolus calculator 22a calculates the working delta bG value according to:

$$Working\_Delta\_bG\_value = \\ -1 \times CarbAmount \times \left(\frac{InsulinSensitivitybG}{InsulinSensitivityInsulin}\right) \times \left(\frac{CarbRatioInsulin}{CarbRatioCarbs}\right)$$

where CarbAmount is the carbohydrate amount value associated with the advice history record and InsulinSensitivitybG, InsulinSensitivityInsulin, CarbRatioInsulin and CarbRatioCarbs are predetermined values provided by the patient or another user in the advice history record. Once the working delta bG value is determined, the working delta bG value is returned and the method 1000 stops executing.

It is appreciated that the foregoing method 1000 is provided for example only and not intended to be limiting. Other techniques for determining the working delta bG value are contemplated and are within the scope of the disclosure.

Figure 13A:
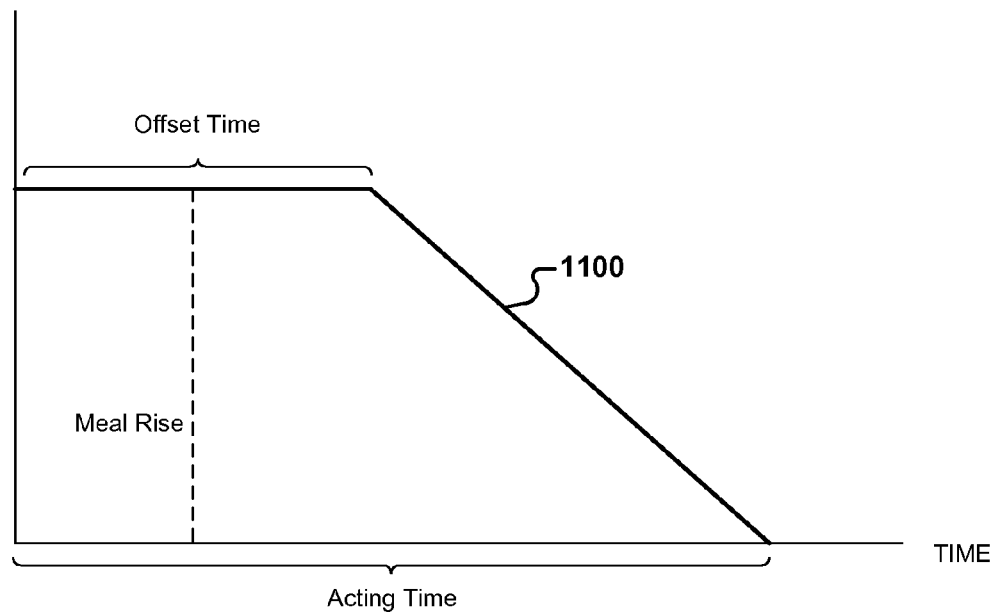
FIGS. 13A and 13B are drawings illustrating an example of a lag time being incorporated to an action shape.
Figure 13B:
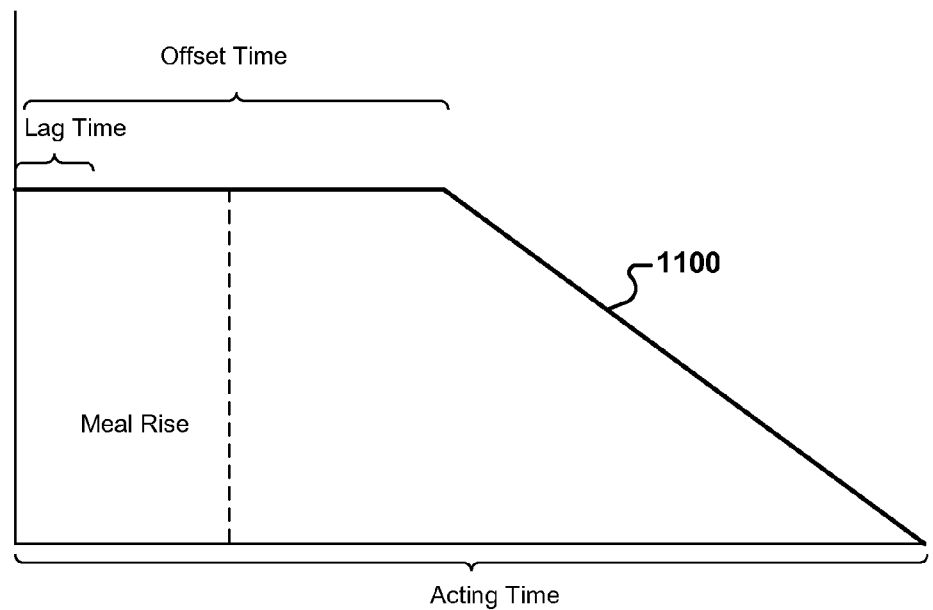

In some embodiments, the patient can provide an indication to the bolus calculator 22a that a dose of insulin will be administered in the near future, e.g., in about 10 minutes. In these embodiments, the bolus calculator 22a can adjust the offset time in the advice history record to compensate for the lag time that will result from the later administered insulin. FIGS. 13A and 13B illustrate an example of lag time being compensated for in such a situation. In FIG. 13A, an action shape 1100 is illustrated. The action shape 1100 of FIG. 13A presumes that the patient will administer insulin at the time of the bolus recommendation. If, however, the patient provides an indication that the insulin will be administered shortly thereafter, the bolus calculator 22a can adjust the offset time and acting time defined in the action shape to account for the lag time between the bolus recommendation and when the insulin will be administered. FIG. 13B illustrates an example of the action shape 1100 after the lag time is accounted for. As should be appreciated, the offset time and the acting time have both been increased by the lag time.

In some embodiments, the patient can turn a bolus advice feature on or off. When the bolus advice feature is turned off, the bolus calculator 22a may be configured not to generate advice history records for various events. If, however, the patient decides to turn the bolus advice feature on, the bolus calculator 22a may require previous advice history records to perform the methods described above. Thus, in some embodiments, when the patient turns the bolus advice feature on, the bolus calculator 22a creates a plurality of advice history records and back-fills the parameter values described above with the values provided by the user, e.g., the patient or the patient's physician. In these embodiments, the various fields may be left empty as the particular data, e.g., bG measurement values and meal histories, to fill the values may not have been recorded. If, however, the data was maintained, the data may be automatically back-filled into the advice history records as well.

In some embodiments, the patient can provide instructions to the insulin pump 36 to deliver a bolus. The user has the option to manually deliver the bolus. When the bolus is administered, the bolus calculator 22a includes the amount of bolus delivered to the patient. A situation may arise however, where the patient is provided with a bolus recommendation, including a recommended amount of insulin, but manually delivers a bolus amount that does not match the recommended amount of insulin. This may be because the patient was unable to enter the precise amount using the user interface of the insulin pump 36 or because of a partial delivery error by the pump. Thus, in some embodiments, the bolus calculator 22a is configured to compare the amount manually entered by the patient as the bolus amount delivered to the bolus recommendation amount. If there is a discrepancy, the bolus calculator 22a determines whether the discrepancy was due to the patient being unable to enter the exact amount using the user interface of the insulin pump 36, e.g., if the amount entered is within a "step-size" of the bolus recommendation. If this is the case, the bolus calculator 22a stores the recommendation accepted as "TRUE" (for example in operation 934). If, however, the amount entered is greater or less than the displayed bolus recommendation, the bolus calculator 22a stores the recommendation accepted as "FALSE" and acts on the amount of insulin manually entered by the patient.

FIGS. 14-17 are activity diagrams which depict exemplary functionality implemented by the graphical user interface of the bolus calculator 22A. Each activity diagram is associated with a respective graphical user interface illustrated in FIGS. 3F-3I. Business rules for each of user interfaces are set forth below. It is understood these rules are exemplary in nature and may vary within the broader aspects of this disclosure.

Figure 14:
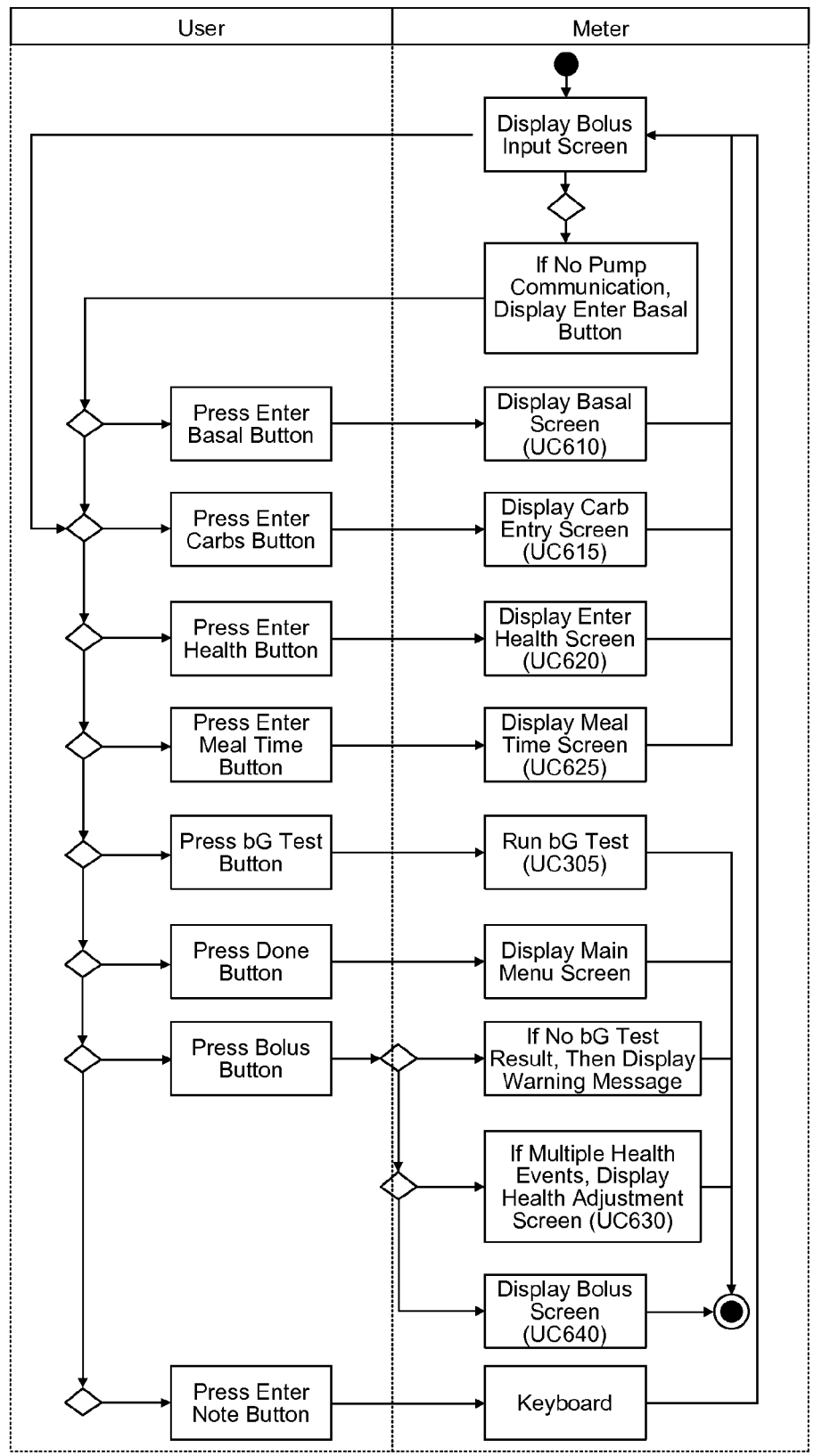
FIG. 14 is an activity diagram depicting exemplary functionality implemented by a bolus input screen of the bolus calculator.

FIG. 14 is an activity diagram for the Bolus Input screen 140 illustrated in FIG. 3F. Various icons may be displayed in the title bar 147 along the top of the Bolus Input screen 140. For example, if the latest bG record has a bG value stored and the record indicates that the meter detected a temperature outside the bG test warning range as defined by the codekey, the meter shall display a temperature icon in the title bar. An expiration time associated with the latest blood glucose measure may also be displayed in the title bar. In one embodiment, the bolus recommendation feature is enabled only for a predefined period of time (e.g., 10 minutes) from the occurrence of the most recent blood glucose measure (also referred to herein as the countdown timer). Once the time period has elapsed, the bolus recommendation feature may be disabled. Thus, this elapsed time or some portion thereof (e.g., last two minutes) may be displayed in the title bar on the various user interfaces associated with the bolus calculator, including those illustrated in FIGS. 3F-3I.

Additionally, the Bolus Input screen 140 presents a listing of items which may serve as input to the bolus calculator. Selection of an item navigates to another screen which enables the user to input the item. For example, selection of the Carbohydrate item 143 leads to an interface for inputting a carbohydrate value; whereas, selection of the Health Events item 144 leads to an interface for selecting health events to associate with the insulin recommendation.

Exemplary rules for displaying the latest blood glucose measure adjacent to the bG Result item 141 are enumerated below. For example, if the previous screen was the Main menu, the meter shall display the blood glucose measure from the latest bG record unless bolus advice is disabled or the record contains a positive User Selected Total Bolus or positive Confirmed Total Bolus or the bG value is LO or Hypo or the record elapsed time is greater than BG_RECORD_EXPIRE_TIME_NOM. If the previous screen was a message indicating the countdown timer has elapsed (i.e., the I_BG_RESULT_EXPIRED screen), the meter shall display the data from the latest bG record. If bolus advice is disabled, the meter shall create a new record, which will become the latest bG record. If the latest bG record contains a positive User Selected Total Bolus or positive Confirmed Total Bolus or the bG value is LO or Hypo or the record elapsed time is greater than BG_RECORD_EXPIRE_TIME_NOM, the meter shall create a new record, which will become the latest bG record. If no bG value is stored in the latest bG record, the meter shall display a button with the bG test icon, the text "bG Test", and the carat icon. If a bG value is stored in the latest bG record, the bG Result Label shall display the bG test icon and the active bG result value, units, and bG value range indicator. If a bG result is not stored in the latest record, the meter shall hide the countdown timer in the title bar. If a bG result is stored in the latest record and the countdown time remaining for the record is greater than the COUNTDOWN_TIMER_EXPIRE_NOM, the meter shall hide the countdown timer in the title bar. If a bG result is stored in the latest record and the record elapsed time is greater than BG_RECORD_EXPIRE_TIME_NOM, the meter shall hide the countdown timer in the title bar. The countdown timer shall be set to BG_RECORD_EXPIRE_TIME_NOM minus (current time–record time stamp). When a bG result is stored in the latest record and the elapsed time of the record is greater than BG_RECORD_EXPIRE_TIME_NOM and the I_BG_RESULT_EXPIRED message has not already been displayed for this result, the meter shall display the I_BG_RESULT_EXPIRED message.

Navigating from the bolus input screen adheres to the following rules. When the meter is paired with a pump, the meter shall hide the Enter Basal Button. When the Enter Basal Button is pressed, the meter shall display the Enter Basal screen. When the Enter Carbs Button is pressed, the meter shall display the Carb Entry screen. When the Enter Health Button is pressed, the meter shall display the Enter Health screen. When the Enter Meal Time Button is pressed, the meter shall display the Meal Time screen. When the bG Test Button is pressed, the meter shall display the Insert Strip screen. When the Enter Note Button is pressed, the meter shall display the Keyboard screen with the value of BG_RECORD_NOTES_VAL displayed in the text field. When the Done Button is pressed, the meter shall return the user to the Main Menu screen.

With regard to the Bolus button, when a bG result is stored in the latest record and the elapsed time of the record is greater than BG_RECORD_EXPIRE_TIME_NOM, the meter shall disable the Bolus Button. When the Bolus Button is pressed and the latest record does not contain a bG result, the meter shall display the I_BOLUS_NO_BG message. If bolus advice is enabled and a bG result is stored in the latest record and the latest bG result is HI and less than or equal to one health event has been selected, when the Bolus Button is pressed, the meter shall display the I_NO_BG_CORRECTION message. When the Bolus Button is pressed and bolus advice is enabled and multiple health events have been selected, the meter shall display the Health Adjustment screen. When the Bolus Button is pressed and the meter is paired to a pump and the pump is paused or stopped, the meter shall display the I_DO_YOU_WANT_TO_START_PUMP message. When the Bolus Button is pressed and Bolus Advice is enabled and the meter is paired to a pump and the meter is not communicating with the pump, the meter shall set the BOLUS_TYPE_VAL equal to Manual and display the M_PUMP_COMM_LOST message. When the Bolus Button is pressed and the meter is paired to a pump and communicating with the pump, the meter shall display the Bolus screen.

Figure 15:
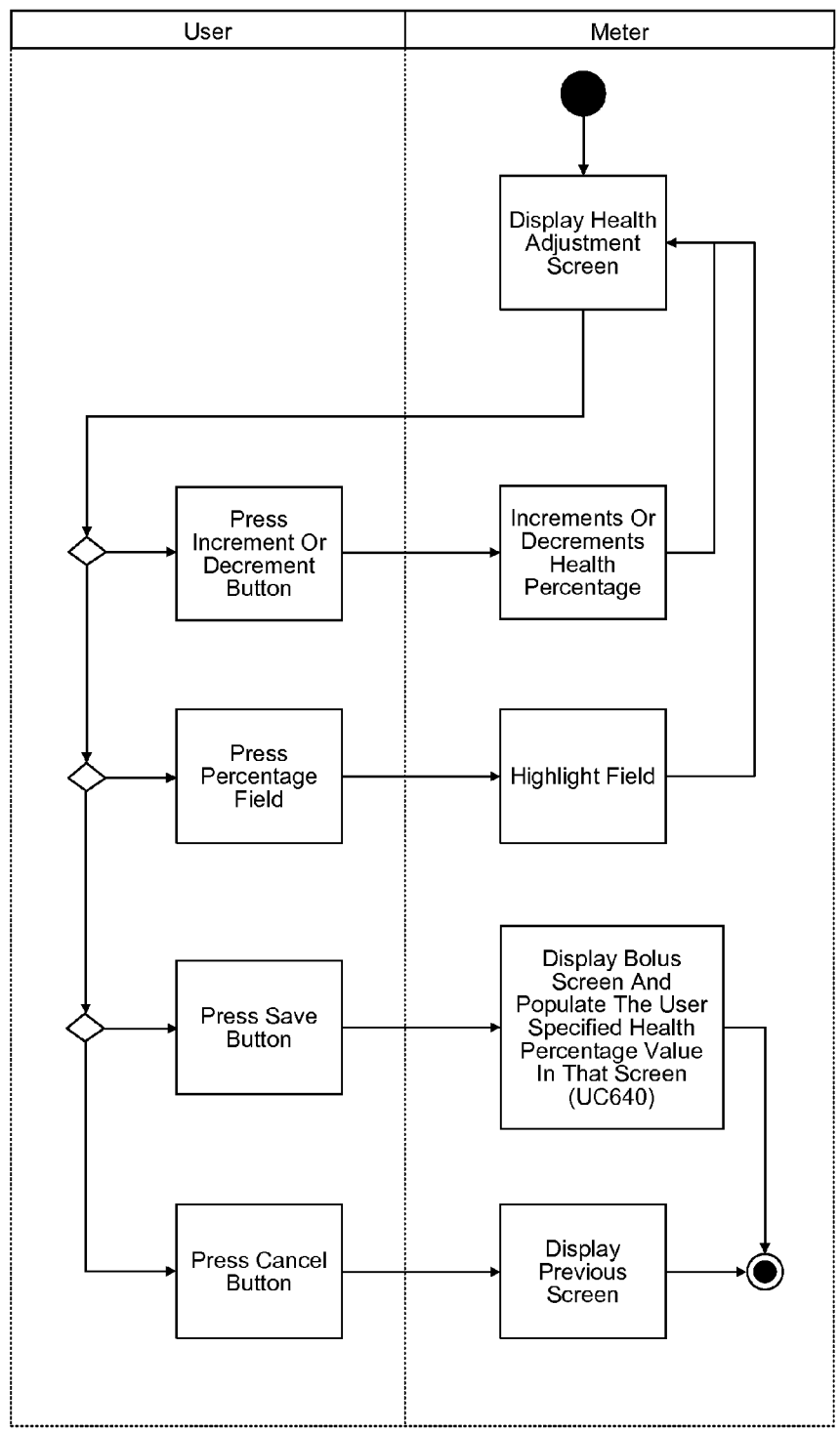
FIG. 15 is an activity diagram depicting exemplary functionality implemented by a health event adjustment screen of the bolus calculator.

FIG. 15 is an activity diagram for the health event adjustment screen illustrated in FIG. 3H. The health event adjustment screen enables the user to enter a percentage adjustment to the insulin recommendation for the selected health events. When the Increment or Decrement Button is pressed, the Percentage Field is highlighted and the meter shall increment or decrement the Percentage Field. When the Save Button is pressed, the meter shall save the value of the BG_RECORD_HEALTH_PERCENT_VAL data definition and display the Bolus screen with the adjusted health percentage value. When the Cancel Button is pressed, the meter shall return the user to the point of entry and discard any changes.

Figure 16:
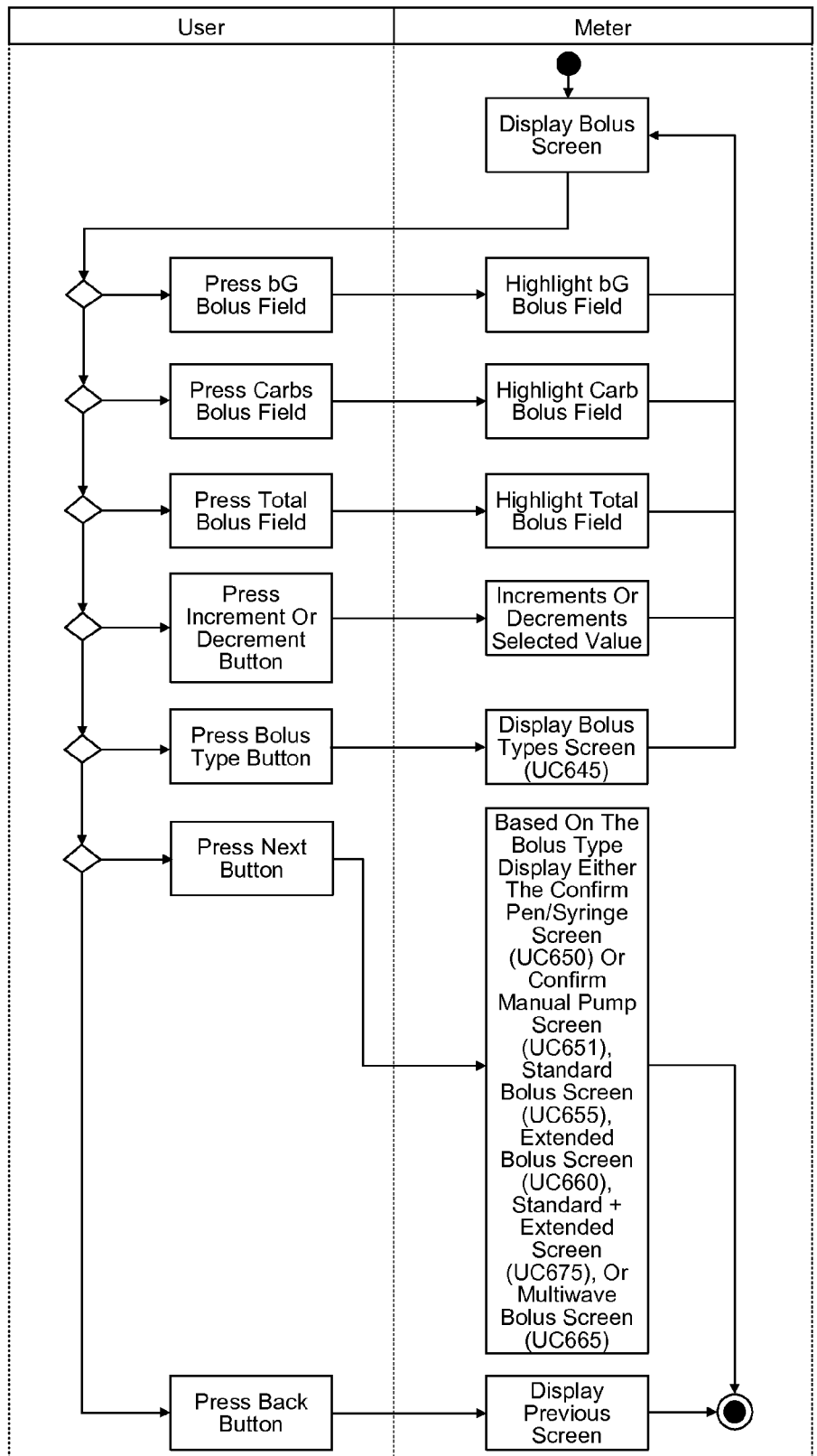
FIG. 16 is an activity diagram depicting exemplary functionality implemented by a bolus screen of the bolus calculator.

FIG. 16 is an activity diagram for the bolus screen illustrated in FIG. 3I. The bolus screen presents an insulin recommendation to the user. More specifically, the insulin recommendation includes a correction amount, a meal amount and a total amount of insulin, where the correction amount is intended to lower a patient's blood glucose level to a target value (also referred to as bG Bolus or Correction Bolus), the meal amount is intended to compensate for carbohydrates consumed by the patient (also referred to as Carb Bolus or Meal Bolus) and the total amount is equal to a sum of the correction amount and the meal amount. Each of these values may be adjusted by the user. Rules governing the display and adjustment of these values are further described below.

Upon initial entry to the Bolus screen, the bG Bolus Field, Carb Bolus Field, and Total Bolus Field shall be enabled. If the latest record includes a bG result and the record indicates that the meter detected a temperature outside the bG test warning range as defined by the codekey, the meter shall display the temperature icon in the title bar. If a bG result is not stored in the latest record, the meter shall hide the countdown timer in the title bar. If a bG result is stored in the latest record and the countdown time remaining for the record is greater than the COUNTDOWN_TIMER_EXPIRE_NOM, the meter shall hide the countdown timer in the title bar. If no bG value is stored in the latest record, the meter shall display in the bG Result Label the bG test icon and the text "No bG Test". If bolus advice is enabled and the max allowed bG value is equal to the center of the target range for the time block of the latest record, the meter shall hide the allowed bG icon and BG_RECORD_MAX_ALLOWED_BG_VAL and units. If bolus advice is disabled, the meter shall hide the Health Value Label. If bolus advice is currently disabled, the meter shall hide the allowed bG icon and the value of BG_RECORD_MAX_ALLOWED_BG_VAL and the units on the second line in the bG Result label. If there are no carbohydrates with the record, the meter shall display "No Entry" in the Carbs Value Label.

Values on the Bolus screen are displayed in accordance with the following exemplary rules. If bolus advice is currently enabled, the meter shall display the bolus advice icon in the title bar and calculate and display values in the bG Bolus Field, Carb Bolus Field, and Total Bolus Field. If the meter is paired with a pump and the recommended Total Bolus is less than 10, then the meter shall populate in the Total Bolus Field the recommended Total Bolus rounded to the nearest 0.05. If the meter is paired with a pump and the recommended Total Bolus is greater than or equal to 10, then the meter shall populate in the Total Bolus Field the recommended Total Bolus rounded to the nearest 0.1. If the meter is not paired with a pump, then the meter shall populate in the Total Bolus Field the recommended Total Bolus rounded to the nearest INSULIN_INC. The meter shall populate in the bG Bolus Field the recommended bG Bolus rounded to the same increment as used for the Total Bolus Field. If the calculated displayed Total Bolus is greater than zero, the meter shall populate the Carb Bolus Field with the value of [Total Bolus–bG Bolus]. If the calculated displayed Total Bolus equals zero, the meter shall populate in the Carb Bolus Field the minimum of the recommended Carb Bolus (rounded to the same increment as used for the Total Bolus Field) or the negative of the displayed bG Bolus. When the bG result is HI, the meter shall display "---" for the bG bolus value. If the meter is paired with a pump and the Total Bolus is less than 10, the meter shall display the bG Bolus, Carb Bolus and Total Bolus fields with two places after the decimal. If the meter is paired with a pump and the Total Bolus is greater than or equal to 10, the meter shall display the bG Bolus, Carb Bolus and Total Bolus fields with one place after the decimal. If the meter is not paired with a pump, the meter shall display the bG Bolus, Carb Bolus and Total Bolus fields according to INSULIN_INC (one place after decimal for 0.5 U, integer value for 1 U).

Total Bolus may be incremented and decremented as follows. If the meter is paired with a pump and the Decrement Button is pressed and Total Bolus is greater than 10, the meter shall decrement the Total Bolus by 0.1. If the meter is paired with a pump and the Decrement Button is pressed and Total Bolus is less than 10, the meter shall decrement the Total Bolus by 0.05. If the meter is paired with a pump and the Increment Button is pressed and the Total Bolus is less than 10, the meter shall increment the Total Bolus by 0.05. If the meter is paired with a pump and the Increment Button is pressed and Total Bolus is greater than or equal to 10, the meter shall increment the Total Bolus by 0.1. If the meter is not paired with a pump, the meter shall increment or decrement Total Bolus by INSULIN_INC. If the Total Bolus Field is edited before the bG Bolus Field or Carb Bolus Field, the meter shall disable the bG Bolus Field and Carb Bolus Field. If the Total Bolus field is highlighted and the Total Bolus does not equal the initially displayed Total Bolus, the meter shall disable the bG Bolus field and the Carb Bolus field. If the Total Bolus field is highlighted and the Total Bolus equals the initially displayed Total Bolus, the meter shall enable the bG Bolus field and the Carb Bolus field. If the bG Bolus Field or the Carb Bolus Field is edited before the Total Bolus Field, the meter shall disable the Total Bolus Field.

When editing the Total Bolus, the bG Bolus and/or Carb Bolus may also be updated. If the Total Bolus Field is highlighted and the Total Bolus equals the initially displayed Total Bolus, the meter shall set the bG Bolus to the initially displayed bG Bolus and the Carb Bolus to the initially displayed Carb Bolus. If the Total Bolus Field is highlighted and the Increment or Decrement Button is pressed and the resulting Total Bolus is greater than the initially displayed Total Bolus, the meter shall set the bG Bolus equal to the (Total Bolus–Carb Bolus). If the Total Bolus Field is highlighted and the Decrement Button is pressed and the resulting Total Bolus is less than the initially displayed bG Bolus, the meter shall set the bG Bolus equal to the Total Bolus. If the Total Bolus Field is highlighted and the Decrement Button is pressed and the resulting Total Bolus is less than the initially displayed Total Bolus and the resulting Total Bolus is greater than or equal to the initially displayed bG Bolus, the meter shall set the Carb Bolus equal to [Total Bolus–bG Bolus]. If the Total Bolus Field is highlighted and the Increment Button is pressed and the resulting Total Bolus is less than or equal to the initially displayed bG Bolus, the meter shall set the bG Bolus equal to the Total Bolus. If the Total Bolus Field is highlighted and the Increment Button is pressed and the resulting Total Bolus is less than the initially displayed Total Bolus and the resulting Total Bolus is greater than the initially displayed bG Bolus, the meter shall set the Carb Bolus equal to the [Total Bolus–bG Bolus].

The bG Bolus may also be incremented and decremented independently. If the meter is paired with a pump and the Decrement Button is pressed and Total Bolus is greater than 10, the meter shall decrement the bG Bolus field by 0.1. If the meter is paired with a pump and the Decrement Button is pressed and Total Bolus is less than 10, the meter shall decrement the bG Bolus field by 0.05. If the meter is paired with a pump and the Increment Button is pressed and the Total Bolus is less than 9.95, the meter shall increment bG Bolus field by 0.05. If the meter is paired with a pump and the Increment Button is pressed and the Total Bolus is equal to 9.95, the meter shall increment bG Bolus to the next tenth of a unit and the meter shall calculate the Carb Bolus as [10.0–bG Bolus]. If the meter is paired with a pump and Increment Button is pressed and Total Bolus is greater than or equal to 10, the meter shall increment bG Bolus field by 0.1. If the meter is not paired with a pump, the meter shall increment or decrement the bG Bolus field by INSULIN_INC.

Likewise, the Carb Bolus field may be incremented or decremented independently. If the meter is paired with a pump and the Decrement Button is pressed and Total Bolus is greater than 10, the meter shall decrement the Carb Bolus field by 0.1. If the meter is paired with a pump and the Decrement Button is pressed and Total Bolus is less than or equal to 10, the meter shall decrement the Carb Bolus field by 0.05. If the meter is paired with a pump and the Increment Button is pressed and the Total Bolus is less than 9.95, the meter shall increment Carb Bolus field by 0.05. If the meter is paired with a pump and the Increment Button is pressed and the Total Bolus is equal to 9.95, the meter shall increment Carb Bolus to the next tenth of a unit and the meter shall calculate the bG Bolus as [10.0–Carb Bolus]. If the meter is paired with a pump and Increment Button is pressed and Total Bolus is greater than or equal to 10, the meter shall increment Carb Bolus field by 0.1. If the meter is not paired with a pump, the meter shall increment or decrement the Carb Bolus field by INSULIN_INC. The meter shall modify the total bolus value to be the greater of [bG Bolus+Carb Bolus] or 0.

Navigating to and from the bolus adjustment screen adheres to the following rules. With regard to the Bolus Type Button, if the meter is not paired with a pump, the meter shall hide the Bolus Type Button and set the bolus type to Pen/Syringe. If the meter is communicating with the pump and the standard bolus is available from the pump, then upon initial entry to the Bolus screen, the meter shall display the Bolus Type Button with the standard bolus icon, set the BOLUS_TYPE_VAL to Standard, and enable the Bolus Type Button. If the meter is communicating with the pump and the standard bolus is NOT available from the pump, then upon initial entry to the Bolus screen, the meter shall display the Bolus Type button with the manual pump icon, set the BOLUS_TYPE_VAL to Manual on Pump, enable the Bolus Type button, and display the I_NO_STD_SET_TO_MANUAL Message. If the meter is paired to a pump and not communicating with the pump, then upon initial entry to the Bolus screen, the meter shall display the Bolus Type Button with the manual pump icon, set the BOLUS_TYPE_VAL to Manual on Pump and enable the Bolus Type Button. If the meter is paired to a pump and communicating with the pump and the pump is paused or stopped, then upon initial entry to the Bolus screen, the meter shall display the Bolus Type Button with the pen/syringe icon, set the BOLUS_TYPE_VAL to Pen/Syringe and enable the Bolus Type Button. If the BOLUS_TYPE_VAL is equal to Standard, the meter shall display in the Bolus Type Button the standard bolus icon. If the BOLUS_TYPE_VAL is equal to Extended, the meter shall display in the Bolus Type Button the extended bolus icon. If the BOLUS_TYPE_VAL is equal to Multiwave, the meter shall display in the Bolus Type Button the multiwave bolus icon. If the BOLUS_TYPE_VAL is equal to Pen/Syringe, the meter shall display in the Bolus Type Button the pen/syringe icon. If the BOLUS_TYPE_VAL is equal to Manual on Pump, the meter shall display in the Bolus Type Button the manual pump icon.

When the Bolus Type Button is pressed, the meter shall display the Bolus Type screen. When the Next Button is pressed and the Total Bolus is equal to 0, the meter shall display the Home screen. When the Next Button is pressed and the meter is not paired with a pump and the Total Bolus is greater than MAX_BOLUS_THRESHOLD_VAL, the meter shall display the I_MAX_BOLUS_HIGH message. When then Next Button is pressed and the Total Bolus is greater than 0 and the bolus type is Pen/Syringe, the meter shall display the I_CONFIRM_PEN_SYRINGE message. When the Next Button is pressed and the Total Bolus is greater than 0 and the bolus type is Manual Pump, the meter shall display the I_CONFIRM_MANUAL_PUMP message. When the Next Button is pressed and the Total Bolus is greater than 0 and the bolus type is Standard and the meter is connected to the pump, the meter shall display the Standard Bolus screen. When the Next Button is pressed and the Total Bolus is greater than 0 and the bolus type is Extended, and the meter is connected to the pump, and the bG Bolus is positive, the meter shall display the I_BOLUS_TYPE_NOT_SUPPORTED message. When the Next Button is pressed and the Total Bolus is greater than 0 and the bolus type is Extended, and the meter is connected to the pump, the meter shall display the Extended Bolus screen. When the Next Button is pressed and the bolus type is Multiwave and the meter is connected to the pump, the meter shall display the Multiwave Bolus screen. When the Next Button is pressed and the bolus type is Standard, Extended, or Multiwave, and the meter is not connected to the pump, the meter shall display the M_PUMP_COMM_LOST message. When the Next Button is pressed and the Total Bolus is greater than 0 and the Carb Bolus is 0 and the Bolus Type is Extended or Multiwave and the meter is connected to the pump, the meter shall display the I_BOLUS_TYPE_NOT_SUPPORTED message. If a bG value is not stored in the latest bG record and a bolus is confirmed by the user, the record's timestamp shall be updated to the time the bolus was confirmed by the user (including pen/syringe and manual pump bolus types). When the Back Button is pressed, the meter shall return the user to the previous screen and discard any changes made on that screen.

Figure 17:
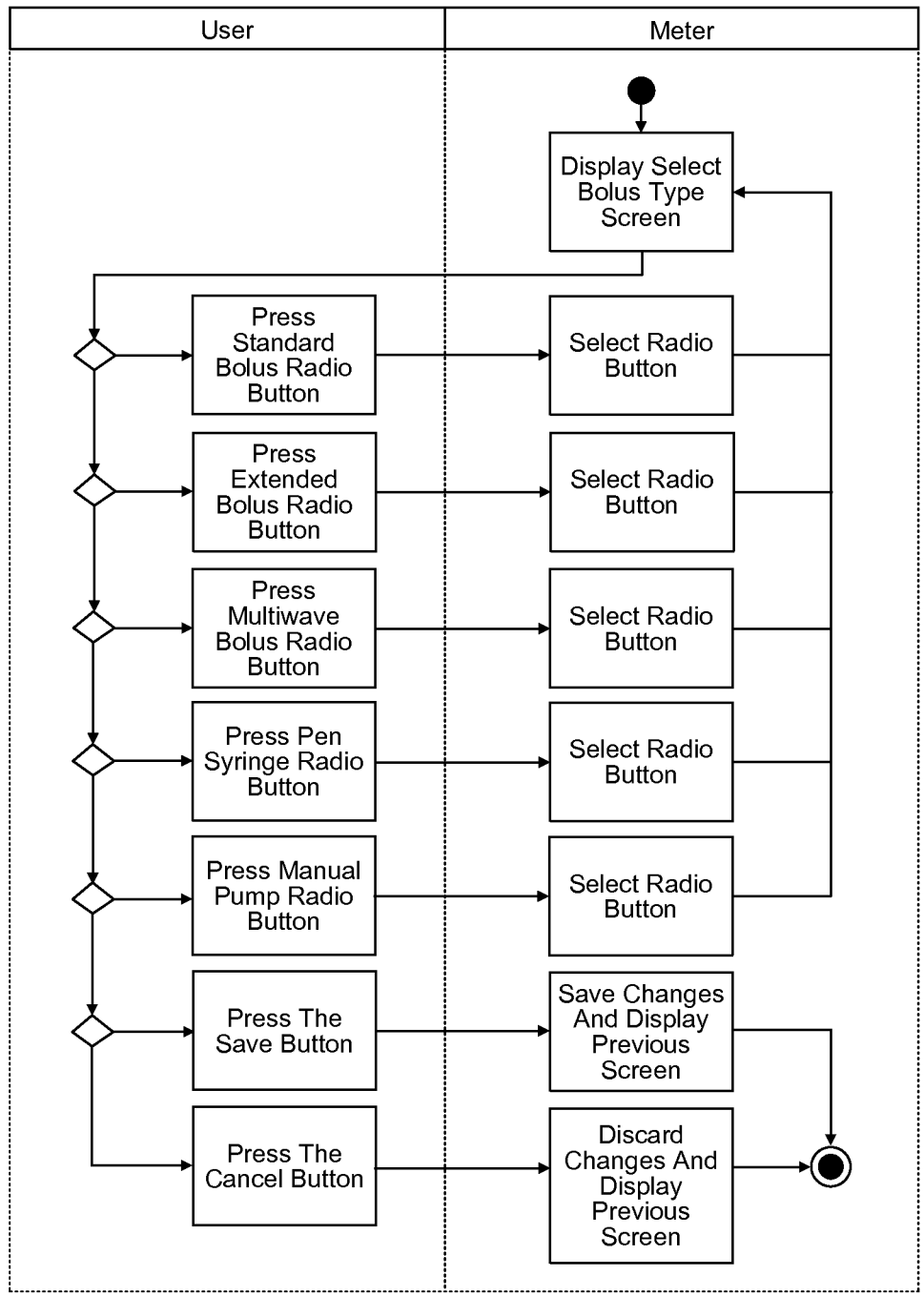
FIG. 17 is an activity diagram depicting exemplary functionality implemented by a bolus type screen of the bolus calculator.

FIG. 17 is an activity diagram for the change bolus type screen illustrated in FIG. 3J. The change bolus type screen present selections for the type of bolus to be administered. In the title bar of this screen, if bolus advice is currently enabled, the meter shall display the bolus advice icon in the title bar; whereas, if bolus advice is currently disabled, the meter shall display the bolus menu icon in the title bar. If a bG result is not stored in the latest record, the meter shall hide the countdown timer in the title bar. If a bG result is stored in the latest record and the countdown time remaining for the record is greater than the COUNTDOWN_TIMER_EXPIRE_NOM, the meter shall hide the countdown timer in the title bar. If a bG result is stored in the latest record and the elapsed time of the bG record is greater than BG_RECORD_EXPIRE_TIME_NOM, the meter shall display the I_BG_RESULT_EXPIRED message.

The enabling of selections available to the user adheres to the following rules. The meter shall enable the Pen Syringe Radio Button. If the meter is communicating with the pump and the Standard Bolus can be run on the pump, the meter shall enable the Standard Bolus Radio Button. If the Standard Bolus, Extended Bolus, and Multiwave Bolus Radio Buttons are all disabled, the meter shall enable the Manual Pump Radio Button. If the meter is communicating with the pump and the Extended Bolus can be run on the pump and a carb correction exists and the bG correction is less than or equal to 0, the meter shall enable the Extended Bolus Radio Button. If the meter is communicating with the pump and the Multiwave Bolus can be run on the pump and a carb correction exists, the meter shall enable the Multiwave Bolus Radio Button. When the Save Button is pressed, the meter shall save the settings and return to the previous screen. When the Cancel Button is pressed, the meter shall return the user to the point of entry and discard any changes.

The techniques described herein may be implemented by one or more computer programs executed by one or more processors. The computer programs include processor-executable instructions that are stored on a non-transitory tangible computer readable medium. The computer programs may also include stored data. Non-limiting examples of the non-transitory tangible computer readable medium are non-volatile memory, magnetic storage, and optical storage.

Some portions of the above description present the techniques described herein in terms of algorithms and symbolic representations of operations on information. These algorithmic descriptions and representations are the means used by those skilled in the data processing arts to most effectively convey the substance of their work to others skilled in the art. These operations, while described functionally or logically, are understood to be implemented by computer programs. Furthermore, it has also proven convenient at times to refer to these arrangements of operations as modules or by functional names, without loss of generality.

Unless specifically stated otherwise as apparent from the above discussion, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system memories or registers or other such information storage, transmission or display devices.

Certain aspects of the described techniques include process steps and instructions described herein in the form of an algorithm. It should be noted that the described process steps and instructions could be embodied in software, firmware or hardware, and when embodied in software, could be downloaded to reside on and be operated from different platforms used by real time network operating systems.

The present disclosure also relates to an apparatus for performing the operations herein. This apparatus may be specially constructed for the required purposes, or it may comprise a general-purpose computer selectively activated or reconfigured by a computer program stored on a computer readable medium that can be accessed by the computer. Such a computer program may be stored in a tangible computer readable storage medium, such as, but is not limited to, any type of disk including floppy disks, optical disks, CD-ROMs, magnetic-optical disks, read-only memories (ROMs), random access memories (RAMs), EPROMs, EEPROMs, magnetic or optical cards, application specific integrated circuits (ASICs), or any type of media suitable for storing electronic instructions, and each coupled to a computer system bus. Furthermore, the computers referred to in the specification may include a single processor or may be architectures employing multiple processor designs for increased computing capability.

The algorithms and operations presented herein are not inherently related to any particular computer or other apparatus. Various general-purpose systems may also be used with programs in accordance with the teachings herein, or it may prove convenient to construct more specialized apparatuses to perform the required method steps. The required structure for a variety of these systems will be apparent to those of skill in the art, along with equivalent variations. In addition, the present disclosure is not described with reference to any particular programming language. It is appreciated that a variety of programming languages may be used to implement the teachings of the present disclosure as described herein.

The present disclosure is well suited to a wide variety of computer network systems over numerous topologies. Within this field, the configuration and management of large networks comprise storage devices and computers that are communicatively coupled to dissimilar computers and storage devices over a network, such as the Internet.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same can also be varied in many ways. Such variations are not to be regarded as a departure from the disclosure, and all such modifications are intended to be included within the scope of the disclosure.

What is claimed is:

1. A computer-implemented method for determining a bolus recommendation which accounts for multiple health events, comprising:
    receiving, by a bolus calculator, a request for an insulin recommendation, where the request includes a blood glucose measure;
    prompting, by the bolus calculator, a user with a health event selection screen to input one or more health events to be associated with the request for an insulin recommendation;
    receiving, by the bolus calculator, indicia for two or more health events to be associated with the request for an insulin recommendation, where the indicia is received on the health event selection screen and in response to prompting the user;
    prompting, by the bolus calculator, the user with a health adjustment screen for an input for the two or more health events associated with the request for an insulin recommendation, where the input represents a cumulative effect of the two or more health events on the insulin recommendation for the user;
    receiving, by the bolus calculator, an input value from the user, where the input is received on the health adjustment screen and in response to prompting the user for an input; and
    computing, by the bolus calculator, the insulin recommendation based in part on the input value received from the user, the bolus calculator implemented by a computer processor of a handheld diabetes management device.

2. The method of claim 1 further comprises computing an insulin recommendation for the patient without prompting for an adjustment value and in response to a determination that only one health event is associated with the request for an insulin recommendation.

3. The method of claim 1 wherein the input value is a percentage such that a value for the insulin recommendation is adjusted in accordance with the percentage.

4. The method of claim 1 further comprises
    receiving, by the bolus calculator, a blood glucose measurement;
    starting a countdown timer in response to the receipt of the blood glucose measurement;
    enabling an insulin recommendation function of the bolus calculator during the countdown timer; and
    disabling the insulin recommendation function of the bolus calculator upon expiration of the countdown timer, where the steps of receiving a blood glucose measurement, starting a countdown timer, enabling an insulin recommendation function and disabling the insulin recommendation function occur before the step of receiving a request for an insulin recommendation.

5. The method of claim 4 further comprises displaying the countdown timer on one or more graphical user interfaces associated with the bolus calculator.

* * * * *